US012562109B2

(12) United States Patent
Kim et al.

(10) Patent No.: US 12,562,109 B2
(45) Date of Patent: Feb. 24, 2026

(54) DISPLAY DEVICE, AND CONTROL METHOD OF DISPLAY DEVICE

(71) Applicant: SAMSUNG DISPLAY CO., LTD., Yongin-si (KR)

(72) Inventors: Sang Ho Kim, Yongin-si (KR); Soo Min Baek, Yongin-si (KR); Ju Youn Son, Yongin-si (KR); Ji Won Lee, Yongin-si (KR); Cheon Myeong Lee, Yongin-si (KR); Bek Hyun Lim, Yongin-si (KR); Ju Hwa Ha, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 301 days.

(21) Appl. No.: 18/191,174

(22) Filed: Mar. 28, 2023

(65) Prior Publication Data

US 2023/0343282 A1 Oct. 26, 2023

(30) Foreign Application Priority Data

Apr. 21, 2022 (KR) ........................ 10-2022-0049253

(51) Int. Cl.
*G09G 3/3208* (2016.01)
*A61B 3/10* (2006.01)
(Continued)

(52) U.S. Cl.
CPC ........... *G09G 3/3208* (2013.01); *A61B 3/101* (2013.01); *A61B 5/01* (2013.01); *A61B 5/1103* (2013.01); *G09G 2354/00* (2013.01)

(58) Field of Classification Search
CPC .... G09G 3/3208; G09G 2354/00; G09G 3/20; G09G 3/3413; A61B 3/101; A61B 5/01;
(Continued)

(56) References Cited

U.S. PATENT DOCUMENTS 11,550,690 B1 * 1/2023 Basu ..................... G06F 3/0484
2005/0094098 A1 * 5/2005 Morita ................ H05B 39/042
351/203
(Continued)

FOREIGN PATENT DOCUMENTS

JP 6821574 1/2021
KR 10-1455714 11/2014
KR 10-1728638 4/2017

OTHER PUBLICATIONS

T.-Y. Su, Z.-Y. Liu and D.-Y. Chen, "Tear Film Break-Up Time Measurement Using Deep Convolutional Neural Networks for Screening Dry Eye Disease," in IEEE Sensors Journal, vol. 18, No. 16, pp. 6857-6862, Aug. 15, 15, 2018, doi: 10.1109/JSEN.2018. 2850940. (Year: 2018).*

(Continued)

*Primary Examiner* — Xiao M Wu
*Assistant Examiner* — Latrell Anthony Creary
(74) *Attorney, Agent, or Firm* — F. CHAU & ASSOCIATES, LLC

(57) ABSTRACT

A display device includes a display member that displays an image, a multi-channel lens unit disposed in a light path of light emitted from the display member, a measurement member that measures a state of an eyeball that is viewing a video output through the multi-channel lens unit, and a processor that controls an intensity of a wavelength of light emitted from the display member by determining the degree of eyeball fatigue based on a measured value of the measurement member.

30 Claims, 27 Drawing Sheets

(51) Int. Cl.
     *A61B 5/01*          (2006.01)
     *A61B 5/11*          (2006.01)
(58) Field of Classification Search
     CPC ... A61B 5/1103; A61B 3/0025; A61B 3/0041;
                    G02B 27/0172; G02B 27/0176; G02B
              27/0093; G02B 2027/014; A61F 9/00736;
                                            A61K 9/08
     See application file for complete search history.

(56)                     References Cited

U.S. PATENT DOCUMENTS

| | | | |
|---|---|---|---|
| 2017/0112667 A1* | 4/2017 | Fateh | A61B 5/1032 |
| 2020/0124845 A1* | 4/2020 | Smith | G09G 5/363 |
| 2023/0301569 A1* | 9/2023 | Gao | A61B 5/163 |
| 2023/0333596 A1* | 10/2023 | Gao | G02B 27/0172 |

OTHER PUBLICATIONS

Young Woo Suh, "The Objective Methods to Evaluate Ocular
Fatigue Associated with Computer Work," Journal of Korean Oph-
thalmological Society, Oct. 15, 2020, pp. 1327-1332.

\* cited by examiner

DD-h: DD-hb, DD-hc, DD-hr

DISPLAY DEVICE, AND CONTROL METHOD OF DISPLAY DEVICE

CROSS-REFERENCE TO RELATED APPLICATION

This application claims priority under 35 U.S.C. 119 from Korean Patent Application No. 10-2022-0049253, filed on Apr. 21, 2022 in the Korean Intellectual Property Office, the contents of which are herein incorporated by reference in their entirety.

TECHNICAL FIELD

Embodiments of the present disclosure are directed to a display device and a control method of a display device.

DISCUSSION OF THE RELATED ART

Display devices include electronic devices that are provided in a form that is wearable on the body. Such electronic devices are commonly referred to as wearable devices. Since wearable electronic devices are directly worn on the body, portability and user's accessibility may be increased.

An example of a wearable electronic device is a head mounted display (HMD) (head mounted electronic device) that can be mounted on a wearer's head portion or head. An HMD may be generally classified as a see-through type that provides augmented reality (AR) and a see-closed type that provides virtual reality (VR).

SUMMARY

Embodiments of the present disclosure provide a display device that can reduce a user's eyeball fatigue.

According to an embodiment, a display device includes a display member that displays an image, a multi-channel lens unit disposed in a light path of light emitted from the display member, a measurement member that measures a state of an eyeball that is viewing a video output through the multi-channel lens unit, and a processor that controlling an intensity of a wavelength of light emitted from the display member by determining the degree of eyeball fatigue based on a measured value of the measurement member.

The measurement member includes a sprayer that sprays a contrast medium, a first wavelength light source disposed outside the multi-channel lens unit and that emits a first wavelength light that increases a transmittance of the contrast medium, and a first wavelength camera sensor disposed outside the multi-lens lens unit. The first wavelength camera sensor generates a first video by receiving the first wavelength light emitted from the first wavelength light source and reflected from a user's eyeball, and measures a tear film breakage time of a user based on the first video.

The processor increases an intensity of a red wavelength of the display member or decreases an intensity of a green wavelength and a blue wavelength of the display member when determining that the degree of eyeball fatigue is high.

The measurement member further includes a second wavelength light source disposed outside the multi-channel lens unit and that emits a second wavelength, and a second wavelength camera sensor disposed outside the multi-channel lens unit. The second wavelength camera sensor generates a second video by receiving the second wavelength light emitted from the second wavelength light source and reflected from the user's eyeball, and detects the number of eye blinks for a preset period based on the second video.

The measurement member further includes a temperature sensor disposed outside the multi-channel lens unit. The temperature sensor measures a temperature of the user's eyeball, and calculates a difference in the temperature of the eyeball for a preset period.

According to an embodiment, display device includes a display member that displays an image, a multi-channel lens unit disposed in a light path of light emitted from the display member, a lens rim that surrounds an edge of the multi-channel lens unit, a sprayer that sprays a contrast medium, a first wavelength light source disposed on the lens rim and that emits a first wavelength light that increases a transmittance of the contrast medium, and a first wavelength camera sensor disposed on the lens rim. The first wavelength camera sensor generates a first video by receiving the first wavelength light emitted from the first wavelength light source and reflected from a user's eyeball, and measures a tear film breakage time of a user based on the first video.

The display device further includes a second wavelength light source disposed on the lens rim and that emits a second wavelength light, and a second wavelength camera sensor disposed on the lens rim. The second wavelength camera sensor generates a second video by receiving the second wavelength light emitted from the second wavelength light source and reflected from the user's eyeball, and detects the number of eye blinks for a preset period based on the second video.

The display device further includes a temperature sensor disposed on the lens rim. The temperature sensor measures a temperature of the user's eyeball, and calculates a temperature difference of the eyeball for a preset period.

According to an embodiment, a method of controlling a display device includes measuring, by a measurement member, a state of an eyeball that is viewing a video output from a display member and displayed through a multi-channel lens unit, determining, by the processor, a degree of eyeball fatigue based on a measured value of the measurement member, and controlling, by the processor, an intensity of light of a wavelength of the display member based on the degree of eyeball fatigue.

Determining, by the processor, the degree of eyeball fatigue based on a measured value of the measurement member includes calculating, by the processor, an eye blink time interval using the number of eye blinks for a preset period, calculating, by the processor, an eye protection index by dividing the tear film breakage time by the eye blink time interval, and determining, by the processor, that the degree of eyeball fatigue is high when the eye protection index is equal to or less than a preset criterion.

The measurement member further includes a second wavelength light source and a second wavelength camera sensor. Measuring the state of the eyeball includes generating, by the second wavelength camera sensor, a second video by receiving a second wavelength light emitted from the second wavelength light source and reflected from the user's eyeball, and detecting, by the second wavelength camera sensor, the number of eye blinks for a preset period based on the second video.

Controlling, by the processor, the intensity of the wavelength of the display member based on the degree of eyeball fatigue includes, when the processor determines that the degree of eyeball fatigue is high, increasing, by the processor, an intensity of a red wavelength of the display member or decreasing an intensity of a green wavelength and a blue wavelength of the display member.

Controlling, by the processor, the intensity of the wavelength of the display member based on the degree of eyeball fatigue includes, when the processor determines that the degree of eyeball fatigue is high, outputting, by the processor, a pre-stored message through an input/output interface that notifies the user that the degree of eyeball fatigue is high and prompts the user for an input, and increasing, by the processor, an intensity of a red wavelength of the display member or decreasing, by the processor, an intensity of a green wavelength and a blue wavelength of the display member.

A display device according to an embodiment can reduce eyeball fatigue.

DETAILED DESCRIPTION

Embodiments will now be described more fully hereinafter with reference to the accompanying drawings. Embodiments may, however, be provided in different forms and should not be construed as limiting. The same reference numbers may indicate the same components throughout the disclosure.

It will also be understood that when a layer is referred to as being "on" another layer or substrate, it can be directly on the other layer or substrate, or intervening layers may also be present.

When an element is referred to as being "connected" or "coupled" to another element, the element may be "directly connected" or "directly coupled" to another element, or "electrically connected" or "electrically coupled" to another element with one or more intervening elements interposed therebetween.

The terms "about" or "approximately" as used herein is inclusive of the stated value and means within an acceptable range of deviation for the particular value as determined by one of ordinary skill in the art, considering the measurement in question and the error associated with measurement of the particular quantity (for example, the limitations of the measurement system.

Figure 1:
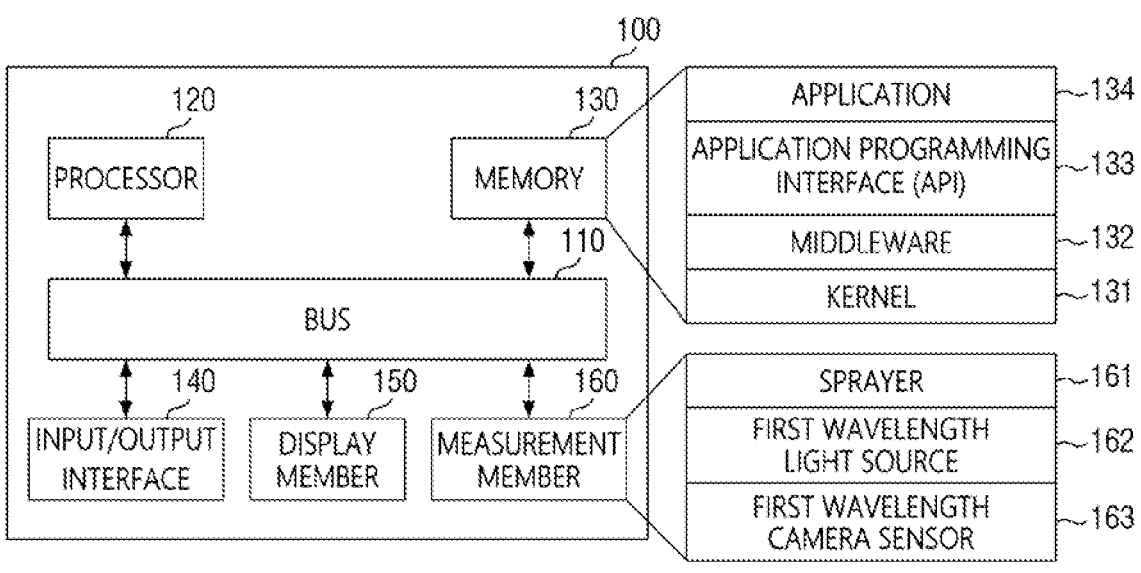
FIG. 1 is a schematic block diagram of a display device according to an embodiment of the present disclosure.
Figure 2:
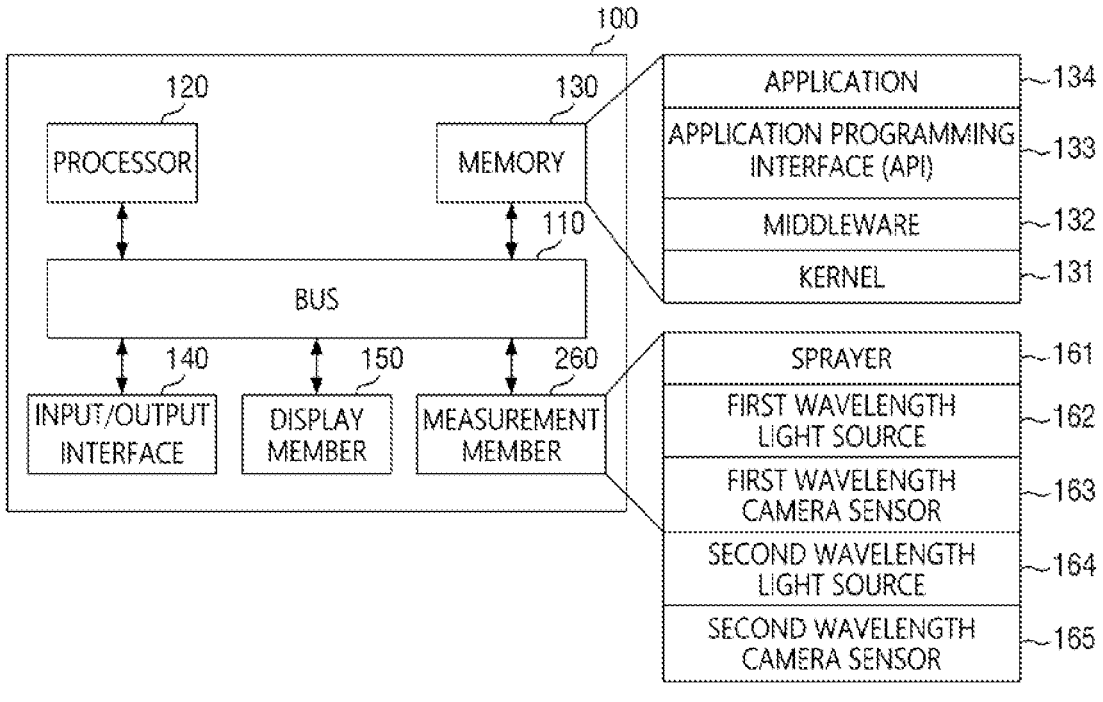
FIG. 2 is a schematic block diagram of a display device according to an embodiment.
Figure 3:
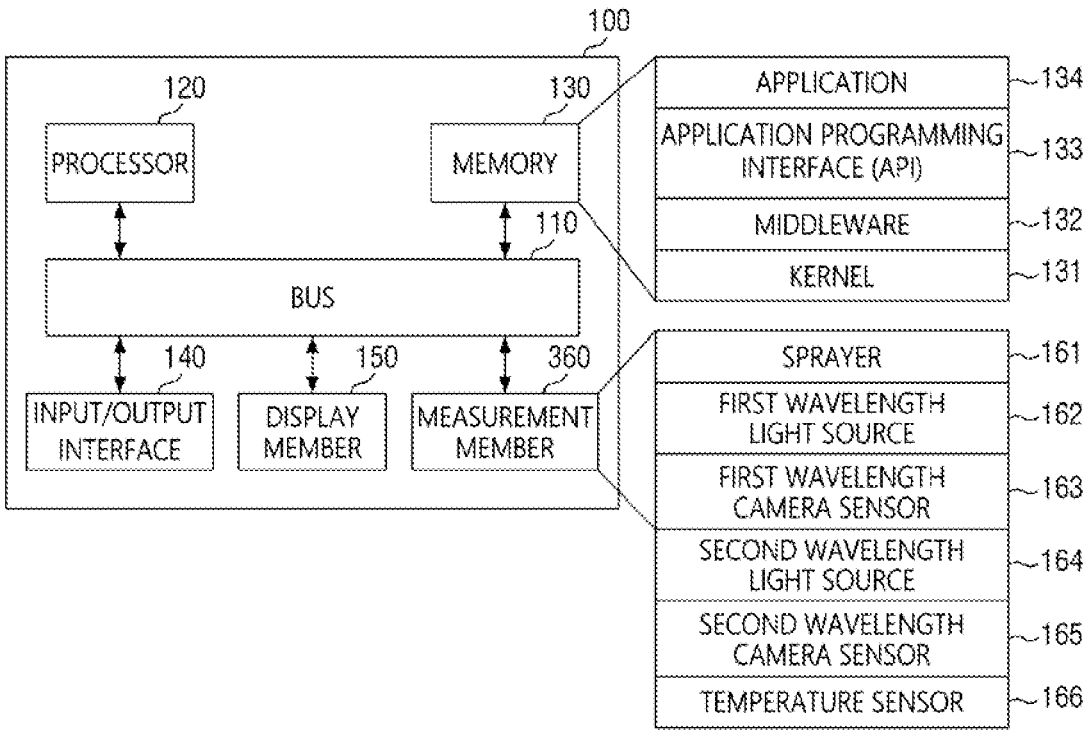
FIG. 3 is a schematic block diagram of a display device according to an embodiment.

FIG. 1 is a schematic block diagram of a display device according to an embodiment, and FIG. 2 is a schematic block diagram of a display device according to another embodiment. FIG. 3 is a schematic block diagram of a display device according to still another embodiment.

Referring to FIG. 1, in an embodiment, a display device 100 includes a bus 110, a processor 120, a memory 130, an input/output interface 140, a display member 150, and a measurement member 160.

The bus 110 is a circuit that connects the aforementioned components to each other and transmits communications, such as control messages, between the aforementioned components.

The processor 120 can, for example, receive requests or data or signals from the aforementioned other components, such as the memory 130, the input/output interface 140, the display member 150, the measurement member 160, etc., via the bus 110, and process operations or data accordingly to control the components.

The processor 120 processes at least some of information obtained from other components, such as the memory 130, the input/output interface 140, the display member 150, the measurement member 160, etc., and provides the processed information to a user in various methods.

In various embodiments, the processor 120 determines the degree of eyeball fatigue according to a measurement value of the measurement member 160, and provides a screen mode that reduces eyeball fatigue according to a determination result. A method for determining the degree of eyeball fatigue will be described below with reference to FIGS. 20 to 24. A screen mode that reduces eyeball fatigue is one in which an output intensity of a specific wavelength of the display member 150 is decreased or increased. In an embodiment, the screen mode that reduces eyeball fatigue is one in which the intensity of wavelengths of 620 nm, 630 nm, 670 nm, and 850 nm is increased. In addition, the screen mode that reduces eyeball fatigue is one in which the intensity of red (R) and infrared (IR) wavelengths of 620 nm, 630 nm, 670 nm, and 850 nm is increased and an intensity of green (G) wavelengths (500 nm to 600 nm) and blue (B) wavelengths (400 nm to 500 nm) is decreased.

The intensity of a specific wavelength is controlled based on pre-stored data on color characteristics according to R, G, and B input voltages of the display member 150. The pre-stored data is pre-stored in the memory 130 in the form of a lookup table.

In an embodiment, the processor 120 provides a menu that is displayed by the display member 150, and provides the eyeball fatigue reducing screen mode when a user's selection is received through the menu.

The memory 130 store commands or data received from the processor 120 or other components or generated by the processor 120 or other components. The memory 130 includes, for example, programming modules such as a kernel 131, middleware 132, an application programming interface (API) 133, or an application 134. Each of the above-described programming modules may be configured by software, firmware, hardware, or a combination of at least two or more thereof.

The kernel 131 controls or manage system resources, such as the bus 110, the processor 120, or the memory 130, used to execute operations or functions implemented in the other programming modules, such as the middleware 132, the API 133, or the application 134. In addition, the kernel 131 provides an interface through which the middleware 132, the API 133, or the application 134 can access and control or manage individual components of the display device 100.

The middleware 132 serves as an intermediary so that the API 133 or the application 134 can communicate with the kernel 131 and exchange data. In addition, the middleware 132 can control work requests, such as scheduling or load balancing, by allocating a priority for using a system resource of the display device 100, such as the bus 110, the processor 120, or the memory 130, to at least one of the applications 134, with respect to the work requests received from the application 134.

The API 133 is an interface for the application 134 to control a function provided by the kernel 131 or the middleware 132, and includes, for example, at least one interface or function, such as an instruction, for file control, window control, image processing, or text control.

According to various embodiments, the application 134 includes an short messaging service/multimedia messaging service (SMS/MMS) application, an email application, a calendar application, an alarm application, a health care application, such as an application that measures exercise or blood glucose, an environment information application, such as an application that provides information on atmospheric pressure, humidity, or temperature, etc.

The input/output interface 140 transmits commands or data received from the user through an input/output device, such as a sensor, a keyboard, or a touch screen, to the processor 120, the memory 130, or the measurement member 160 through, for example, the bus 110. For example, the input/output interface 140 provides data on a user's touch input through the touch screen to the processor 120. In addition, the input/output interface 140 can, for example, output through an input/output device, such as a speaker or a display member, the command or data received from the processor 120 and the memory 130 through the bus 110. For example, the input/output interface 140 can output voice data processed through the processor 120 to the user through a speaker. For another example, the input/output interface 140 can output a message processed through the processor 120 to the user through the display member 150.

The display member 150 (or the display module) can display various types of information, such as multimedia data, text data, etc., to the user. For example, the display member 150 includes a display panel, such as a liquid crystal display (LCD) panel or an organic light-emitting diode (OLED) panel, and a display driver IC (DDI). The DDI can display color by adjusting pixels of the display panel. For example, the DDI includes a circuit that converts a digital signal into an RGB analog value and transmits the RGB analog value to the display panel.

According to an embodiment, the display member 150 includes an organic light emitting diode (OLED) panel, but is not necessarily limited thereto. The OLED panel includes a panel circuit that implements a color of pixel areas (or pixels). The panel circuit includes a plurality of OLED light emitting elements arranged on a screen, and each of the OLED light emitting elements forms a pixel. The OLED light emitting element has a structure in which an organic light emitting material is deposited between a cathode electrode and an anode electrode. A current flows through the organic light emitting material between the two electrodes, and the organic light emitting material emits light through an electroluminescence phenomenon.

The OLED panel implements color by using a three color (red, green, and blue) independent pixel method, a color conversion method (CCM), a color filter method, etc. For example, the OLED panel expresses a dot, which is a unit that expresses one color, with a combination of OLED light emitting elements that include three colors, such as red, green, and blue.

The OLED panel may be one of a passive matrix organic light emitting diodes (PMOLED) panel or an active matrix organic light emitting diodes (AMOLED) panel. For example, the AMOLED panel includes a built-in thin film transistor (TFT) for each AMOLED light emitting element and individually controls whether each AMOLED light emitting element emits light. For example, when a forward voltage is applied to the thin film transistor, the current flows through the organic light emitting material at a certain threshold voltage or more, and the organic light emitting material emits light. For example, as the amount of current flowing through the organic light emitting material increases, the organic light emitting material emits brighter light. Conversely, when a reverse voltage is applied to the thin film transistor, little current flows through the organic light emitting material, and the organic light emitting material does not emit light.

The OLED panel includes a plurality of pixel areas and a black matrix area. Each of the plurality of pixel areas is a minimum unit forming an image. Each of the plurality of pixel areas generally has the same shape and are regularly arranged side by side in a row direction (e.g., X-axis direction) or a column direction (e.g., Y-axis direction), but embodiments are not necessarily limited thereto. One dot, which is a unit for expressing one color, forms a pixel group that includes pixel areas, such as a red pixel area, a green pixel area, and a blue pixel area, that can emit light of one of three colors, such as red, green, or blue. The pixel group, such as three pixel areas, are repeatedly arranged in the row direction (e.g., the X-axis direction) or the column direction (e.g., the Y-axis direction). In addition, the number of pixel areas that the pixel group includes is not limited to three, and in some embodiment, the pixel group includes more than three pixel areas. The above-described organic light emitting material is disposed in the pixel areas. The black matrix area is separated from the pixel areas, and divides the pixel areas. For example, the black matrix area includes a color filter or a separator that separates the AMOLED light emitting elements. At least a portion of the above-described thin film transistor and a circuit related thereto, such as the OLED panel circuit that implements the color of the pixel, is disposed in the black matrix area.

The measurement member 160 includes a sprayer 161 that sprays a contrast medium, a first wavelength light source 162 that emits light of a first wavelength, and a first wavelength camera sensor 163 that detects the light of the first wavelength and outputs a video signal.

The sprayer 161 sprays the contrast medium from an inner container in the form of mist at a preset cycle or a non-periodic cycle. The contrast medium may be fluorescein, but is not necessarily limited thereto, and any contrast medium that is safe for human eyes and can directly or indirectly measure the degree of eyeball fatigue is sufficient. For reference, when fluorescein is sprayed into the eye, epithe-lial cells of a damaged cornea are dyed. When light of a specific wavelength is illuminated on the dyed cornea, cracks in a green fluorescent film appear. A tear film break-age time can be measured based on the time at which the cracks in the green fluorescent film appear after fluorescein is sprayed into the eye. When the tear film breakage time is shorter than a preset reference time, it is interpreted that the degree of eyeball fatigue is high.

The first wavelength light source 162 emits light that has a first wavelength that increases a transmittance of the contrast medium. For example, the first wavelength is a cobalt blue wavelength in the range of 430 nm to 480 nm.

The first wavelength camera sensor 163 generates a first video by receiving the light of the first wavelength emitted from the first wavelength light source and reflected from a user's eyeball. The first wavelength camera sensor 163 measures the tear film breakage time of the user by detecting a luminance and a color of the first video.

As illustrated in FIG. 2, in an embodiment, the measure-ment member 260 includes the sprayer 161, the first wave-length light source 162 that emits light of the first wave-length, the first wavelength camera sensor 163 that generates the first video by detecting the light of the first wavelength and measures the tear film breakage time of the user based on the first video, and further includes a second wavelength light source 164 that emits of light of a second wavelength, and a second wavelength camera sensor 165 that generates a second video by detecting the light of the second wave-length, and detects and outputs the number of eye blinks for a preset period based on the second video. For example, the second wavelength is an infrared wavelength in the range of 780 nm to 1000 nm.

As illustrated in FIG. 3, in an embodiment, the measure-ment member 360 includes the sprayer 161, the first wave-length light source 162, the first wavelength camera sensor 163, the second wavelength light source 164, and the second wavelength camera sensor 165, and further includes a tem-perature sensor 166 that measures a temperature of the eyeball. The temperature sensor 166 is a non-contact type temperature sensor. For example, the temperature sensor 166 is an infrared thermometer, but is not necessarily limited thereto.

In an embodiment, the measurement member further includes the second wavelength light source 164 that emits light of the second wavelength, the second wavelength camera sensor 165 that generates the second video by detecting light of the second wavelength, and detects and outputs the number of eye blinks for a preset period based on the second video, and a temperature sensor 166 that measures the eyeball temperature and calculates a tempera-ture difference of the eyeball for a preset period.

Figure 4:
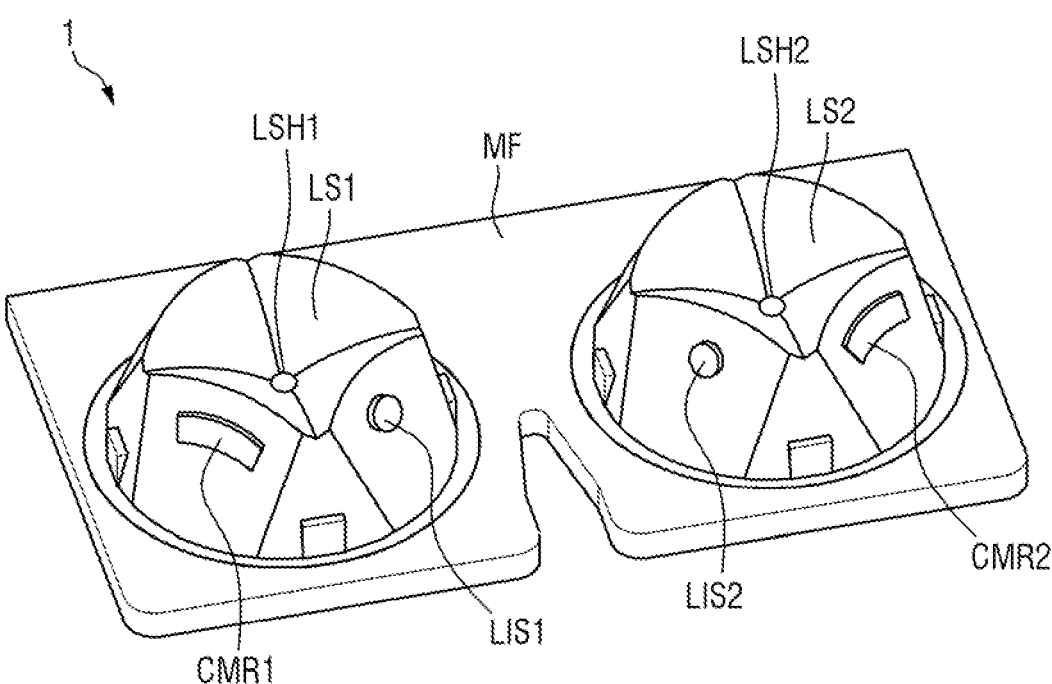
FIG. 4 is a perspective view of a display device according to an embodiment.
Figure 4:
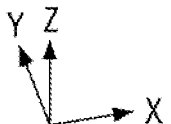
Figure 5:
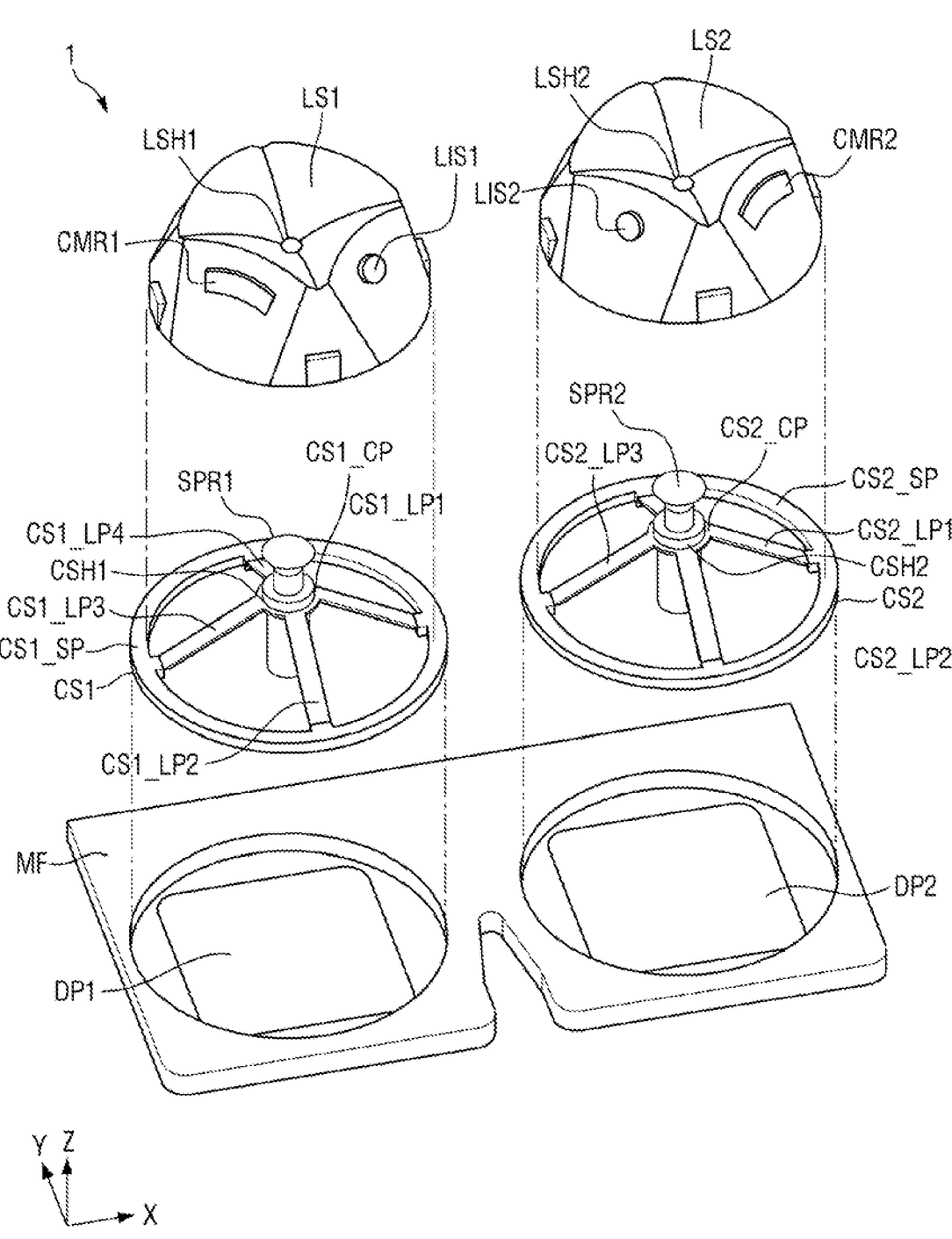
FIG. 5 is an exploded perspective view of a display device according to an embodiment.

FIG. 4 is a perspective view of a display device according to an embodiment, and FIG. 5 is an exploded perspective view of a display device according to an embodiment.

Hereinafter, a first direction X, a second direction Y, and a third direction Z intersect each other in different directions. For example, the first direction X is a length direction, the second direction Y is a width direction, and the third direction Z is a thickness direction. The third direction Z is a direction in which the user's eyeball is positioned or a direction in which images of a first display member DP1 and a second display member DP2 to be described below are displayed. However, the directions and names are relative, and are not necessarily limited to the examples.

The following display device 1 includes a head mounted display device mounted on a user's head and that provides a screen on which an image or a video is displayed to the user.

The head mounted display device may be a see-through type that provides augmented reality based on actual exter-nal objects, or a see-closed type that provides virtual reality to the user through a screen independent of external objects. Hereinafter, a see-closed type head mounted display device is described as an example, but embodiments of the present disclosure are not necessarily limited thereto.

Referring to FIGS. 4 and 5, in an embodiment, the display device 1 includes a main frame MF, a first display member DP1, a second display member DP2, a first multi-channel lens LS1, a second multi-channel lens LS2, a first holding member CS1, a second holding member CS2, a first sprayer SPR1, a second sprayer SPR2, a first light source LIS1, a second light source LIS2, a first camera sensor CMR1, and a second camera sensor CMR2. Each of the first sprayer SPR1 and the second sprayer SPR2 corresponds to the sprayer 161 of FIGS. 1-3.

The main frame MF is worn on a user's face. The main frame MF has a shape that corresponds to a shape of a user's head or face. In an embodiment, the main frame MF has a shape similar to that of glasses, but is not necessarily limited thereto.

The main frame MF includes the first display member DP1, the second display member DP2, the first multi-channel lens LS1, the second multi-channel lens LS2, the first holding member CS1, the second holding member CS2, the first sprayer SPR1, and the second sprayer SPR2 mounted thereon. In some embodiments, the main frame MF further includes a structure such as a strap or a belt for facilitating mounting. In some embodiments, a control unit, a video processing unit, and a lens receiving unit are further mounted on the main frame MF.

The first display member DP1 and the second display member DP2 display an image and/or a video. Light that provides the image and/or the video is emitted from the first display member DP1 and the second display member DP2.

The first display member DP1 and the second display member DP2 are fixed to the main frame MF, and are detachably provided on the main frame MF. The first display member DP1 and the second display member DP2 may be opaque, transparent, or translucent depending on a design of the display device 1, such as a type of the display device 1. The first display member DP1 and the second display member DP2 include an electronic component such as a display module that includes a display panel to be described below or a display device 1 such as a mobile terminal that includes a display panel, but embodiments are not neces-sarily limited thereto.

Each of the first display member DP1 and the second display member DP2 includes a display panel that displays an image or a video.

In an embodiment, the display panel is a light emitting display panel that includes a light emitting element. For example, the display panel in one of an organic light emitting display panel that uses an organic light emitting diode that includes an organic light emitting layer, a micro light emitting diode (LED) display panel that uses micro LEDs, a quantum dot light emitting display panel that uses a quantum dot light emitting diode that includes a quantum dot light emitting layer, or an inorganic light emitting display panel that uses an inorganic light emitting element that includes an inorganic semiconductor, but embodiments are not necessarily limited thereto.

In an embodiment, the display device 1 is provided with two display members spaced apart from each other so as to respectively correspond to each eye of the user, but embodiments of the present disclosure are not necessarily limited thereto. In some embodiments, the first display member DP1 and the second display member DP2 are replaced with one display member that overlaps both the first multi-channel lens LS1 and the second multi-channel lens LS2.

The first multi-channel lens LS1 and the second multi-channel lens LS2 transmit to the user light emitted from the first display member DP1 or the second display member DP2, respectively.

The first multi-channel lens LS1 and the second multi-channel lens LS2 reflect and/or refract the light emitted from the first display member DP1 and the second display member DP2 and provide the reflected and/or refracted light to the user. The first multi-channel lens LS1 and the second multi-channel lens LS2 provide a plurality of channels through which the light emitted from the first display member DP1 and the second display member DP2 passes. The plurality of channels transmit the light emitted from the first display member DP1 and the second display member DP2 through different paths and to the user. The light emitted from the first display member DP1 and the second display member DP2 is incident on each of the channels and an enlarged image is focused on the user's eye. The plurality of channels are implemented by a plurality of sub-lenses LS11, LS12, LS13, LS14, LS21, LS22, LS23, and LS24, shown in FIG. 6, and a plurality of reflective lenses RL11, RL12, RL13, and RL14, shown in FIG. 7, that are described below.

The first multi-channel lens LS1 is disposed on the first display member DP1, and the second multi-channel lens LS2 is disposed on the second display member DP2. The first multi-channel lens LS1 and the second multi-channel lens LS2 are disposed at positions corresponding to user's left and right eyes, respectively.

The first multi-channel lens LS1 covers the first holding member CS1. The second multi-channel lens LS2 covers the second holding member CS2. Detailed configurations of the first multi-channel lens LS1 and the second multi-channel lens LS2 will be described below with reference to FIGS. 6 to 8 and 15A.

The first holding member CS1 and the second holding member CS2 are disposed on the first display member DP1 and the second display member DP2, respectively. The first holding member CS1 is disposed between the first display member DP1 and the first multi-channel lens LS1, and the second holding member CS2 is disposed between the second display member DP2 and the second multi-channel lens LS2. The first holding member CS1 holds the first sprayer SPR1, and the second holding member CS2 holds the second sprayer SPR2. The first sprayer SPR1 and the second sprayer SPR2 are detachably disposed on the first holding member CS1 and the second holding member CS2 to charge a contrast medium for the first sprayer SPR1 and the second sprayer SPR2.

The first sprayer SPR1 and the second sprayer SPR2 are held by the first holding member CS1 and the second holding member CS2, respectively, and overlap the first multi-channel lens LS1 and the second multi-channel lens LS2. Thus, an internal space of the display device 1 is efficiently used, and an overall volume of the display device 1 is reduced.

The first multi-channel lens LS1 has a first lens hole LSH1 formed in a central portion thereof. The contrast medium sprayed by the first sprayer SPR1 is discharged in the form of mist through the first lens hole LSH1.

The second multi-channel lens LS2 has a second lens hole LSH2 formed in a central portion thereof. The contrast medium sprayed by the second sprayer SPR2 is discharged in the form of mist through the second lens hole LSH2.

The first display member DP1, the first holding member CS1, the first sprayer SPR1, and the first multi-channel lens LS1 overlap each other in the third direction Z. The second display member DP2, the second holding member CS2, the second sprayer SPR2, and the second multi-channel lens LS2 overlap each other in the third direction Z. The third direction Z is a direction in which the user's eyeball is positioned.

The first light source LIS1 and the first camera sensor CMR1 are disposed outside the first multi-channel lens LS1. The second light source LIS2 and the second camera sensor CMR2 are disposed outside the second multi-channel lens LS2. The first light source LIS1 and the second light source LIS2 emit light IRL that has the first wavelength to one object, such as the user's eyeball. The first camera sensor CMR1 and the second camera sensor CMR2 include various cameras that can detect the first wavelength light reflected from the object, or a photoelectric conversion element such as an image sensor that detects light and generates electric charge. Data generated by the first camera sensor CMR1 and the second camera sensor CMR2 is used as a basis for determining the degree of eyeball fatigue. In an embodiment, the first light source LIS1 and the first camera sensor CMR1 are integrally formed, and the second light source LIS2 and the second camera sensor CMR2 are integrally formed.

The display device 1 further includes a control unit that controls an overall operation of the display device 1.

The control unit controls operations of the first sprayer SPR1, the second sprayer SPR2, the first light source LIS1, the first camera sensor CMR1, the second light source LIS2, and the second camera sensor CMR2. The control unit controls spraying cycles of the first sprayer SPR1 and the second sprayer SPR2. The control unit can shorten the spraying cycle as a video viewing time increases.

The control unit determines the degree of eyeball fatigue based on the data generated by the first camera sensor CMR1 and the second camera sensor CMR2. An algorithm for determining the degree of eyeball fatigue by the control unit will be described below with reference to FIGS. 18 to 24.

The control unit may be implemented as, for example, a dedicated processor that includes an embedded processor and/or a general-purpose processor that includes a central processing device or an application processor, but embodiments are not necessarily limited thereto.

Figure 6:
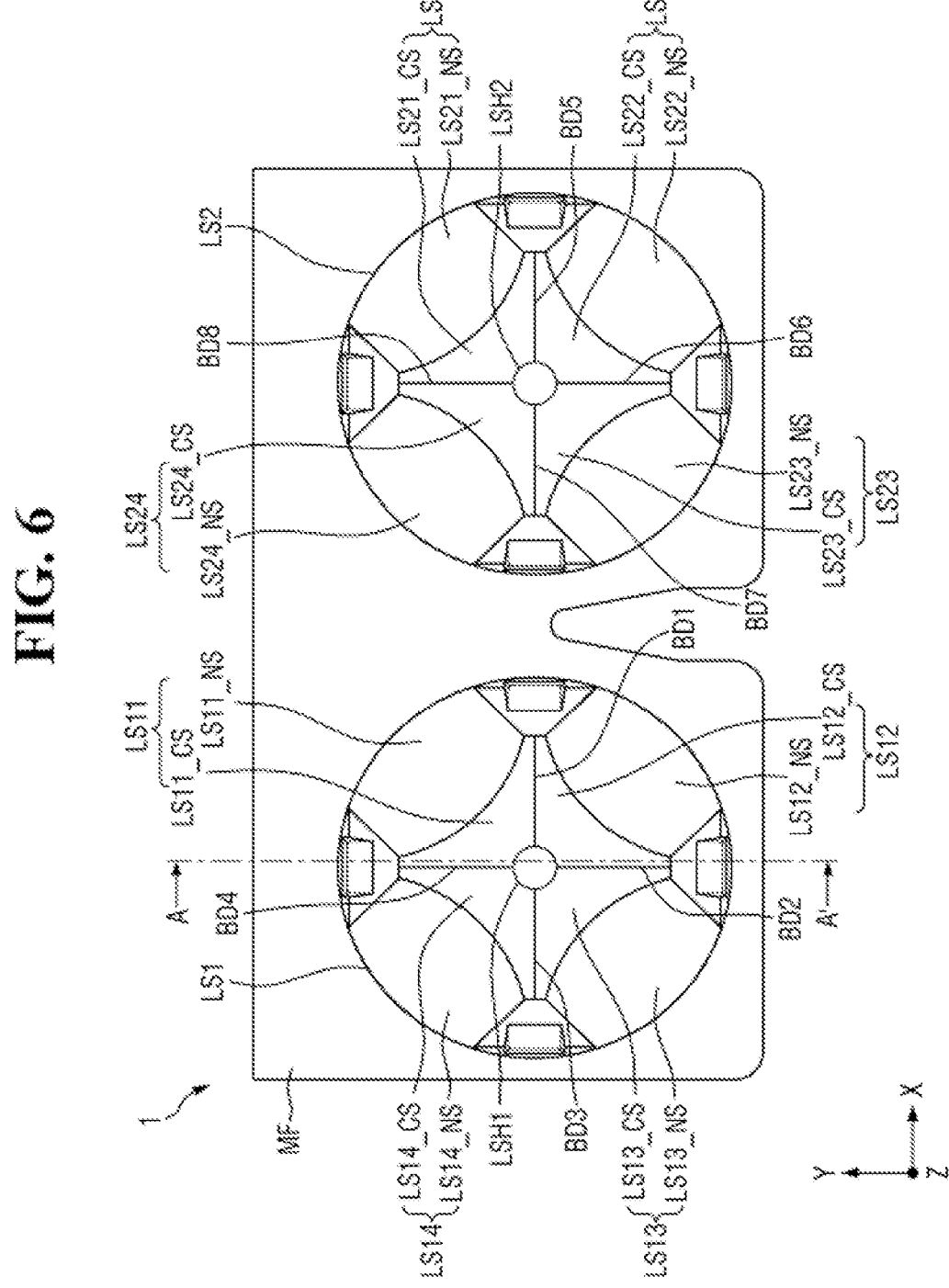
FIG. 6 is a plan view of a display device according to an embodiment.
Figure 7:
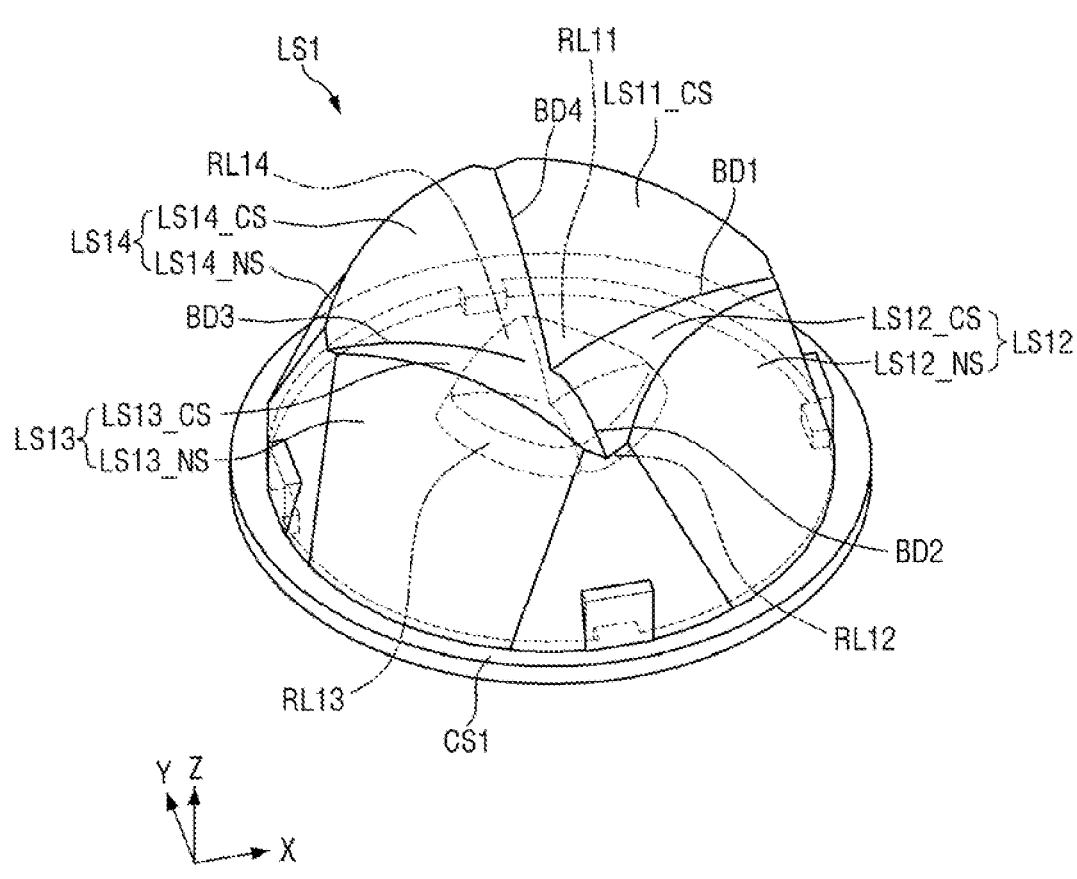
FIG. 7 is a perspective view of a first multi-channel lens according to an embodiment.
Figure 8:
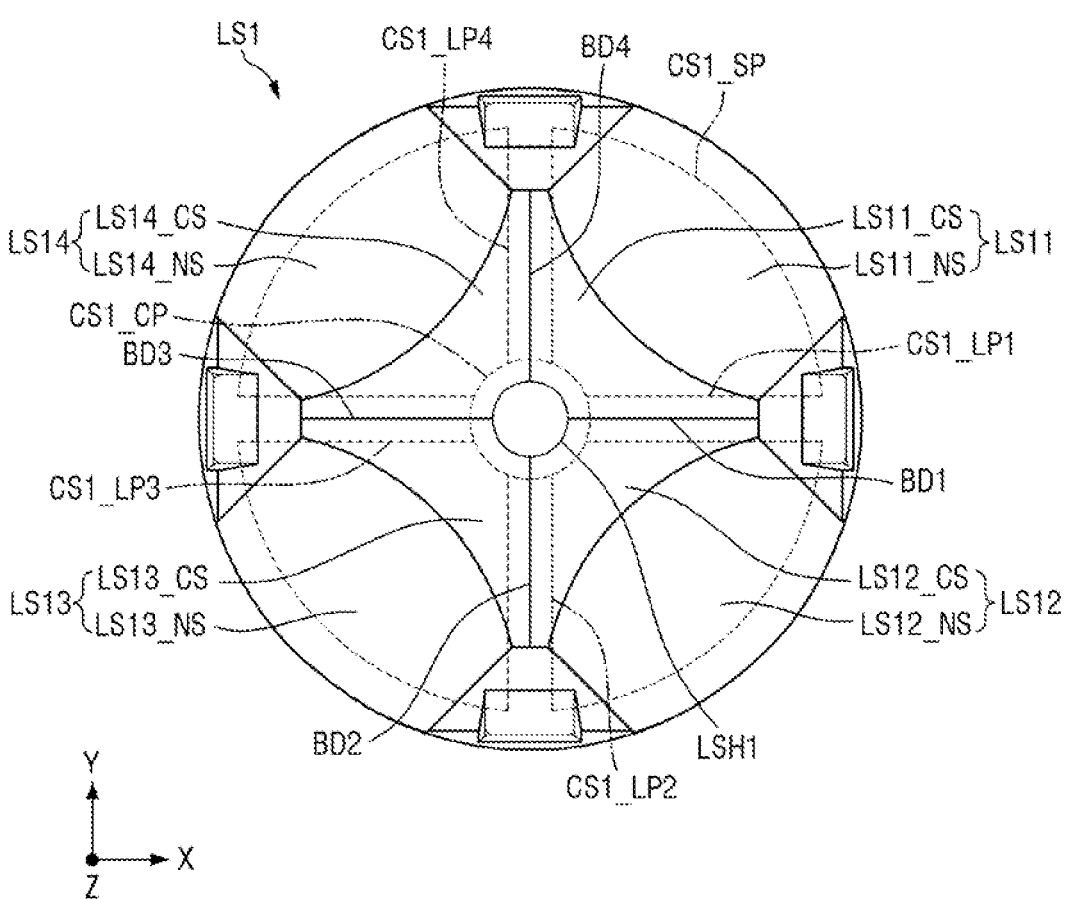
FIG. 8 is a plan view of a first multi-channel lens according to an embodiment.

FIG. 6 is a plan view of a display device according to an embodiment. FIG. 7 is a perspective view of a first multi-channel lens according to an embodiment. FIG. 8 is a plan view of the first multi-channel lens according to an embodiment.

Referring to FIGS. 6 to 8, in an embodiment, the first multi-channel lens LS1 and the second multi-channel lens LS2 are respectively positioned at positions that correspond to each eye of the user. For example, the first multi-channel lens LS1 and the second multi-channel lens LS2 are symmetrically disposed with respect to an imaginary axis in the second direction Y that perpendicularly bisects a line segment that connects the first multi-channel lens LS1 and the second multi-channel lens LS2 with the shortest distance. The first multi-channel lens LS1 and the second multi-channel lens LS2 have substantially the same or similar shape and structure. The first multi-channel lens LS1 and the second multi-channel lens LS2 have an approximately circular shape in a plan view, but the shape of the first multi-channel lens LS1 and the second multi-channel lens LS2 in a plan view is not necessarily limited thereto.

The first multi-channel lens LS1 and the second multi-channel lens LS2 include a plurality of sub-lenses LS11, LS12, LS13, LS14, LS21, LS22, LS23, and LS24, respectively. The plurality of sub-lenses LS11, LS12, LS13, LS14, LS21, LS22, LS23, and LS24 may respectively provide a plurality of channels through which the light emitted from the first display member DP1 or the second display member DP2 passes.

In an embodiment, the first multi-channel lens LS1 and the second multi-channel lens LS2 each include four sub-lenses LS11, LS12, LS13, and LS14, and LS21, LS22, LS23, and LS24, respectively, but the number of sub-lenses LS11, LS12, LS13, LS14, LS21, LS22, LS23, and LS24 included in one multi-channel lens LS1 or LS2 is not necessarily limited thereto. In some embodiments, the first multi-channel lens LS1 and the second multi-channel lens LS2 include three or fewer sub-lenses, respectively, or include five or more sub-lenses, respectively.

Hereinafter, for convenience of description, based on the center of the first multi-channel lens LS1, the sub-lens LS11 positioned at an upper right end, the sub-lens LS12 positioned at a lower right end, the sub-lens LS13 positioned at a lower left end, and the sub-lens LS14 positioned at an upper left lend will be referred to as a first sub-lens LS11, a second sub-lens LS12, a third sub-lens LS13, and a fourth sub-lens LS14, respectively. In addition, based on the center of the second multi-channel lens LS2, the sub-lens LS21 positioned at an upper right end, the sub-lens LS22 positioned at a lower right end, the sub-lens LS23 positioned at a lower left end, and the sub-lens LS24 positioned at an upper left lend will be referred to as a fifth sub-lens LS21, a sixth sub-lens LS22, a seventh sub-lens LS23, and an eighth sub-lens LS24, respectively.

Referring to FIGS. 6 to 8, in an embodiment, the plurality of sub-lenses LS11, LS12, LS13, LS14, LS21, LS22, LS23, and LS24 in the first multi-channel lens LS1 or the second multi-channel lens LS2 are symmetric with respect to the center of the first multi-channel lens LS1 or the center of the second multi-channel lens LS2. For example, the first sub-lens LS11, the second sub-lens LS12, the third sub-lens LS13, and the fourth sub-lens LS14 are symmetric with respect to the center of the first multi-channel lens LS1. The fifth sub-lens LS21, the sixth sub-lens LS22, the seventh sub-lens LS23, and the eighth sub-lens LS24 are symmetric with respect to the center of the second multi-channel lens LS2.

The plurality of sub-lenses LS11, LS12, LS13, LS14, LS21, LS22, LS23, and LS24 in the first multi-channel lens LS1 or the second multi-channel lens LS2 are integrally connected to each other. For example, the first sub-lens LS11, the second sub-lens LS12, the third sub-lens LS13, and the fourth sub-lens LS14 are machined to be integrally connected to form one first multi-channel lens LS1, and the fifth sub-lens LS21, the sixth sub-lens LS22, the seventh sub-lens LS23, and the eighth sub-lens LS24 are machined to be integrally connected to form one second multi-channel lens LS2. For example, one sub-lens refers to a specific portion or a specific area that provides one channel of the first multi-channel lens LS1 or the second multi-channel lens LS2. However, embodiments of the present disclosure are not necessarily limited thereto, and in some embodiments, the first multi-channel lens LS1 and the second multi-channel lens LS2 are lens assemblies that include the plurality of sub-lenses LS11, LS12, LS13, LS14, LS21, LS22, LS23, and LS24 separated from each other.

Each of the plurality of sub-lenses LS11, LS12, LS13, LS14, LS21, LS22, LS23, and LS24 includes at least one outer surface that faces the user's eyeball.

For example, the first sub-lens LS11 includes a first outer surface LS11_NS and a second outer surface LS11_CS, the second sub-lens LS12 includes a third outer surface LS12_NS and a fourth outer surface LS12_CS, the third sub-lens LS13 includes a fifth outer surface LS13_NS and a sixth outer surface LS13_CS, and the fourth sub-lens LS14 includes a seventh outer surface LS14_NS and an eighth outer surface LS14_CS. The fifth sub-lens LS21 includes a ninth outer surface LS21_NS and a tenth outer surface LS211_CS, the sixth sub-lens LS22 includes an eleventh outer surface LS22_NS and a twelfth outer surface LS22_CS, the seventh sub-lens LS23 includes a thirteenth outer surface LS23_NS and a fourteenth outer surface LS23_CS, and the eighth sub-lens LS24 includes a fifteenth outer surface LS24_NS and a sixteenth outer surface LS24_CS.

As described above, the second multi-channel lens LS2 is substantially the same as or similar to the first multi-channel lens LS1. In an embodiment, since the first outer surface LS11_NS, the second outer surface LS11_CS, the third outer surface LS12_NS, the fourth outer surface LS12_CS, the fifth outer surface LS13_NS, the sixth outer surface LS13_CS, the seventh outer surface LS14_NS, and the eighth outer surface LS14_CS are substantially same as or similar to the ninth outer surface LS21_NS, the tenth outer surface LS21_CS, the eleventh outer surface LS22_NS, the twelfth outer surface LS22_CS, the thirteenth outer surface LS23_NS, the fourteenth outer surface LS23_CS, the fifteenth outer surface LS24_NS, and the sixteenth outer surface LS24_CS, respectively, hereinafter, the first outer surface LS11_NS, the second outer surface LS11_CS, the third outer surface LS12_NS, the fourth outer surface LS12_CS, the fifth outer surface LS13_NS, the sixth outer surface LS13_CS, the seventh outer surface LS14_NS, and the eighth outer surface LS14_CS will be mainly described.

The first outer surface LS11_NS, the third outer surface LS12_NS, the fifth outer surface LS13_NS, and the seventh outer surface LS14_NS extend from an edge of the first multi-channel lens LS1 toward the center of the first sub-lens LS11. The first outer surface LS11_NS, the third outer surface LS12_NS, the fifth outer surface LS13_NS, and the seventh outer surface LS14_NS protrude in a third direction Z away from a plane of the main frame MF upon which the first multi-channel lens LS1 is mounted. The first outer surface LS11_NS, the third outer surface LS12_NS, the fifth outer surface LS13_NS, and the seventh outer surface LS14_NS are inclined in the third direction Z. The inclination of first outer surface LS11_NS, the third outer surface LS12_NS, the fifth outer surface LS13_NS, and the seventh outer surface LS14_NS is such that a width of the first multi-channel lens LS1 in the first direction X or the second direction Y becomes narrower the further the first multi-channel lens LS1 extends from the main frame MF. In an embodiment, each of the first outer surface LS11_NS, the third outer surface LS12_NS, the fifth outer surface LS13_NS, and the seventh outer surface LS14_NS is a flat inclined surface, but embodiments are not necessarily limited thereto. In some embodiments, each of the first outer surface LS11_NS, the third outer surface LS12_NS, the fifth outer surface LS13_NS, and the seventh outer surface LS14_NS is also a curved surface.

The second outer surface LS11_CS, the fourth outer surface LS12_CS, the sixth outer surface LS13_CS, and the eighth outer surface LS14_CS extend from the first outer surface LS11_NS, the third outer surface LS12_NS, the fifth outer surface LS13_NS, and the seventh outer surface LS14_NS, respectively, toward the center of the first multi-channel lens LS1. The first lens hole LSH1 is formed at a contact point of the second outer surface LS11_CS, the fourth outer surface LS12_CS, the sixth outer surface LS13_CS, and the eighth outer surface LS14_CS, at the center of the first multi-channel lens LS1, in a plan view. The second outer surface LS11_CS, the fourth outer surface LS12_CS, the sixth outer surface LS13_CS, and the eighth outer surface LS14_CS surround the first lens hole LSH1 formed at the center of the first multi-channel lens LS1. The second outer surface LS11_CS, the fourth outer surface LS12_CS, the sixth outer surface LS13_CS, and the eighth outer surface LS14_CS are interconnected in a clockwise direction based on the center of the first multi-channel lens LS1. However, embodiments of the present disclosure are not necessarily limited thereto, and the second outer surface LS11_CS, the fourth outer surface LS12_CS, the sixth outer surface LS13_CS, and the eighth outer surface LS14_CS may also be interconnected in a counterclockwise direction based on the center of the first multi-channel lens LS1.

The second outer surface LS11_CS, the fourth outer surface LS12_CS, the sixth outer surface LS13_CS, and the eighth outer surface LS14_CS are inclined in the third direction Z. The second outer surface LS11_CS, the fourth outer surface LS12_CS, the sixth outer surface LS13_CS, and the eighth outer surface LS14_CS are inclined to the first outer surface LS11_NS, the third outer surface LS12_NS, the fifth outer surface LS13_NS, and the seventh outer surface LS14_NS, respectively. As illustrated in FIG. 7, an edge of a portion where the first outer surface LS11_NS and the second outer surface LS11_CS are connected, an edge of a portion where the third outer surface LS12_NS and the fourth outer surface LS12_CS are connected, an edge of a portion where the fifth outer surface LS13_NS and the sixth outer surface LS13_CS are connected, and an edge of a portion where the seventh outer surface LS14_NS and the eighth outer surface LS14_CS are connected protrudes in the third direction Z or an outer direction, but embodiments of the present disclosure are not necessarily limited thereto. The second outer surface LS11_CS, the fourth outer surface LS12_CS, the sixth outer surface LS13_NS, and the eighth outer surface LS14_CS are inwardly inclined in the third direction Z from the edges with the first, third, fifth and seventh outer surfaces LS11_NS, LS12_NS, LS13_NS and LS14_NS, respectively, toward the plane of the main frame MF upon which the first multi-channel lens LS1 is mounted.

The second outer surface LS11_CS, the fourth outer surface LS12_CS, the sixth outer surface LS13_CS, and the eighth outer surface LS14_CS face the third direction Z. Each of the second outer surface LS11_CS, the fourth outer surface LS12_CS, the sixth outer surface LS13_CS, and the eighth outer surface LS14_CS may be referred to as an eyepiece surface or a front surface that faces the user's eyeball. Each of the first outer surface LS11_NS, the third outer surface LS12_NS, the fifth outer surface LS13_NS, and the seventh outer surface LS14_NS may be referred to as a side surface that is connected to the second outer surface LS11_CS, the fourth outer surface LS12_CS, the sixth outer surface LS13_CS, or the eighth outer surface LS14_CS, respectively, and does not face the user's eyeball.

In an embodiment, each of the second outer surface LS11_CS, the fourth outer surface LS12_CS, the sixth outer surface LS13_CS and the eighth outer surface LS14_CS includes a flat surface, but is not necessarily limited thereto. In some embodiments, each of the second outer surface LS11_CS, the fourth outer surface LS12_CS, the sixth outer surface LS13_CS, and the eighth outer surface LS14_CS has a convex surface that convexly protrudes in the third direction Z.

At least one lens boundary is formed between the plurality of sub-lenses LS11, LS12, LS13, LS14, LS21, LS22, LS23, and LS24 in the first multi-channel lens LS1 or the second multi-channel lens LS2. For example, when the first multi-channel lens LS1 and the second multi-channel lens LS2 each have four sub-lenses (four channels), a lens boundary that has a cross shape on a plane forms in each of the first multi-channel lens LS1 and the second multi-channel lens LS2. However, the shape of the lens boundary is not necessarily limited thereto, and the shape of the lens boundary can vary according to the design of the display device 1.

Referring to FIGS. 6 to 8, in an embodiment, the lens boundary of the first multi-channel lens LS1 includes a first lens boundary BD1, a second lens boundary BD2, a third lens boundary BD3, and a fourth lens boundary BD4, and the lens boundary of the second multi-channel lens LS2 includes a fifth lens boundary BD5, a sixth lens boundary BD6, a seventh lens boundary BD7, and an eighth lens boundary BD8.

For the first multi-channel lens LS1, the first lens boundary BD1 is formed between the second outer surface LS11_CS and the fourth outer surface LS12_CS, the second lens boundary BD2 is formed between the fourth outer surface LS12_CS and the sixth outer surface LS13_CS, the third lens boundary BD3 is formed between the sixth outer surface LS13_CS and the eighth outer surface LS14_CS, and the fourth lens boundary BD4 is formed defined between the eighth outer surface LS14_CS and the second outer surface LS11_CS. As illustrated in FIG. 7, the first lens boundary BD1, the second lens boundary BD2, the third lens boundary BD3, and the fourth lens boundary BD4 are valleys portions between the second outer surface LS11_CS, the fourth outer surface LS12_CS, the sixth outer surface LS13_CS, and the eighth outer surface LS14_CS, but are not necessarily limited thereto. For example, in some embodiments, when the first outer surface LS11_NS, the third outer surface LS12_NS, the fifth outer surface LS13_NS, and the seventh outer surface LS14_NS are interconnected, the lens boundary further include boundaries between the first outer surface LS11_NS, the third outer surface LS12_NS, the fifth outer surface LS13_NS, and the seventh outer surface LS14_NS.

Similarly, for the second multi-channel lens LS2, the fifth lens boundary BD5 is formed between the tenth outer surface LS21_CS and the twelfth outer surface LS22_CS, the sixth lens boundary BD6 is formed between the twelfth outer surface LS22_CS and the fourteenth outer surface LS23_CS, the seventh lens boundary BD7 is formed between the fourteenth outer surface LS23_CS and the sixteenth outer surface LS24_CS, and the eighth lens boundary BD8 is formed between the sixteenth outer surface LS24_CS and the tenth outer surface LS21_CS. The fifth lens boundary BD5, the sixth lens boundary BD6, the seventh lens boundary BD7, and the eighth lens boundary BD8 are substantially the same as or similar to the first lens boundary BD1, the second lens boundary BD2, the third lens boundary BD3, and the fourth lens boundary BD4, respectively.

The first multi-channel lens LS1 further includes reflective lenses RL11, RL12, RL13, and RL14. The reflective lenses RL11, RL12, RL13, and RL14 will be described below with reference to FIG. 15A.

Since the display device 1 has a symmetrical structure that corresponds to the eyes of the user, and since the second multi-channel lens LS2, the second holding member CS2, and the second sprayer SPR2 are substantially the same as or similar to the first multi-channel lens LS1, the first holding member CS1, and the first sprayer SPR1, respectively, hereinafter, the first multi-channel lens LS1, the first holding member CS1, and the first sprayer SPR1 will be mainly described.

Figure 9:
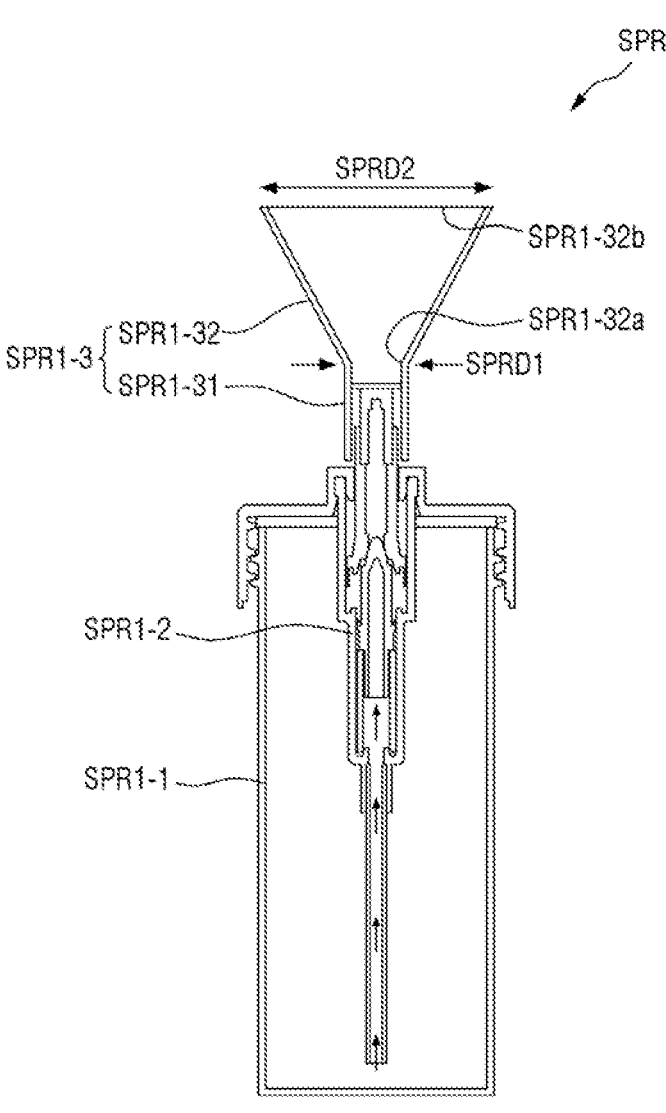
FIG. 9 is a perspective view of a sprayer according to an embodiment.
Figure 10:
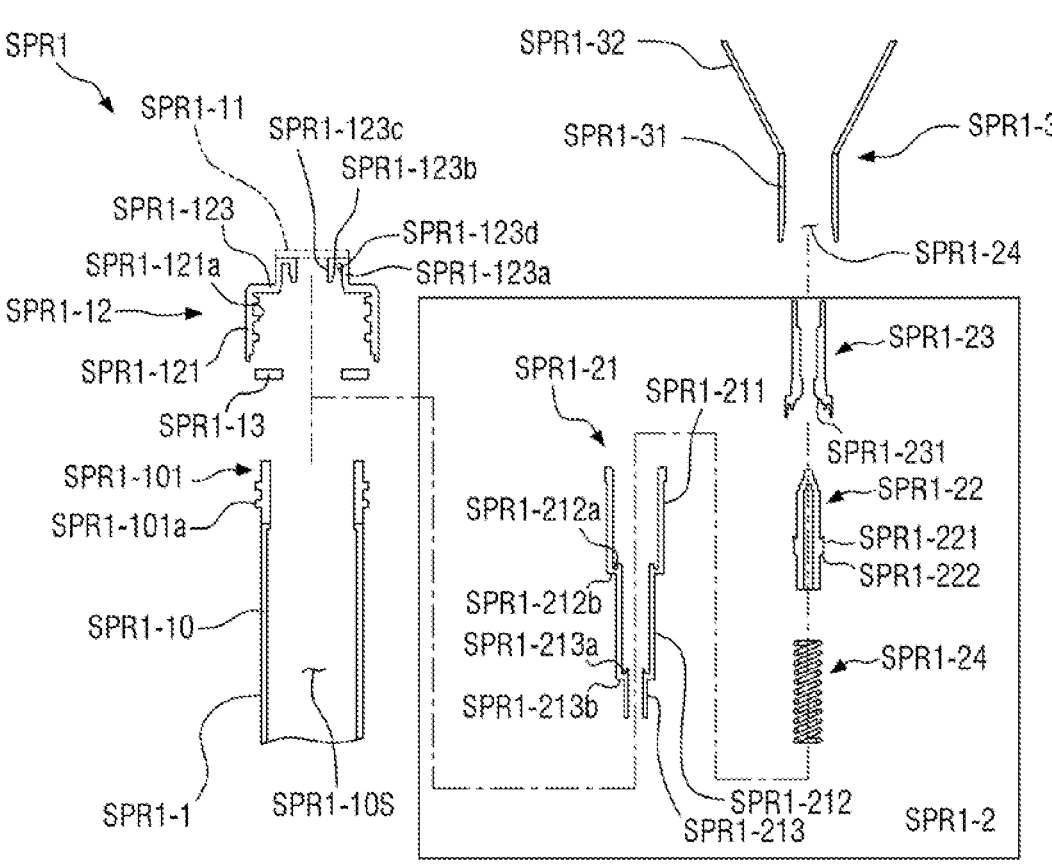
FIG. 10 is an exploded perspective view of a sprayer according to an embodiment.
Figure 11:
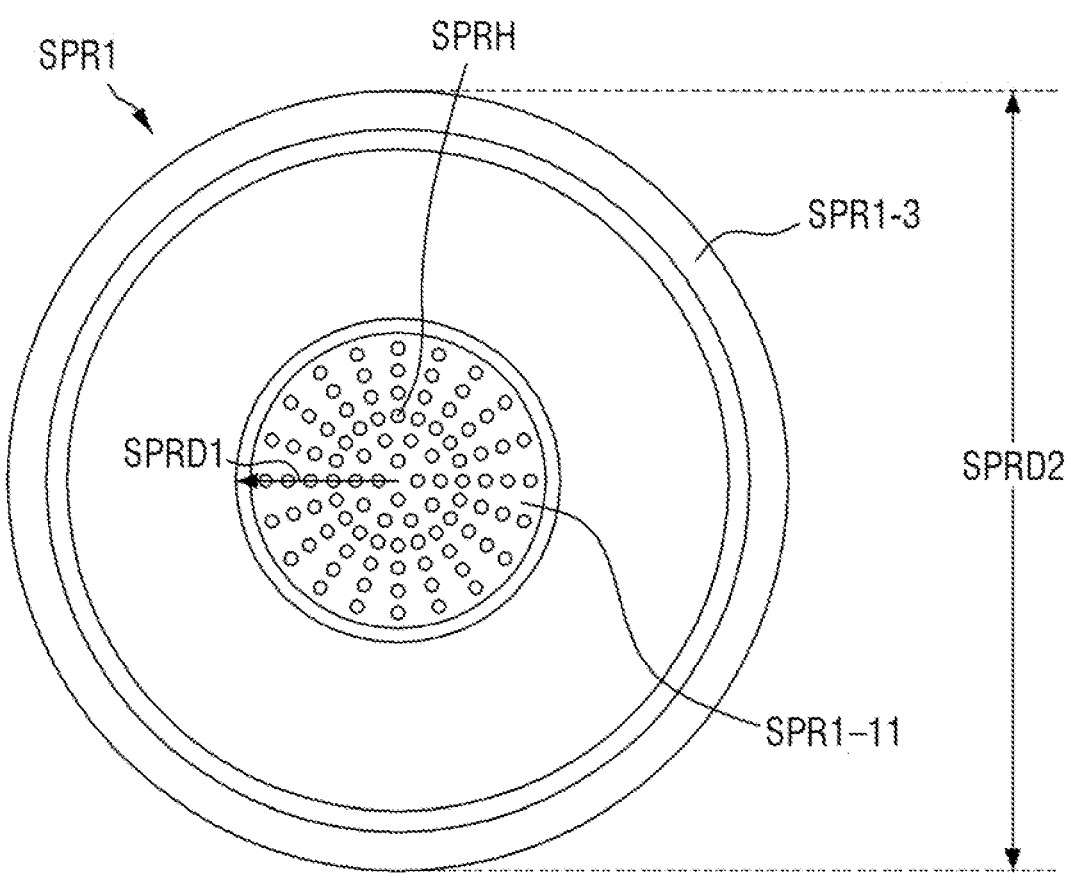
FIG. 11 is a plan view of the sprayer according to an embodiment.
Figure 12:
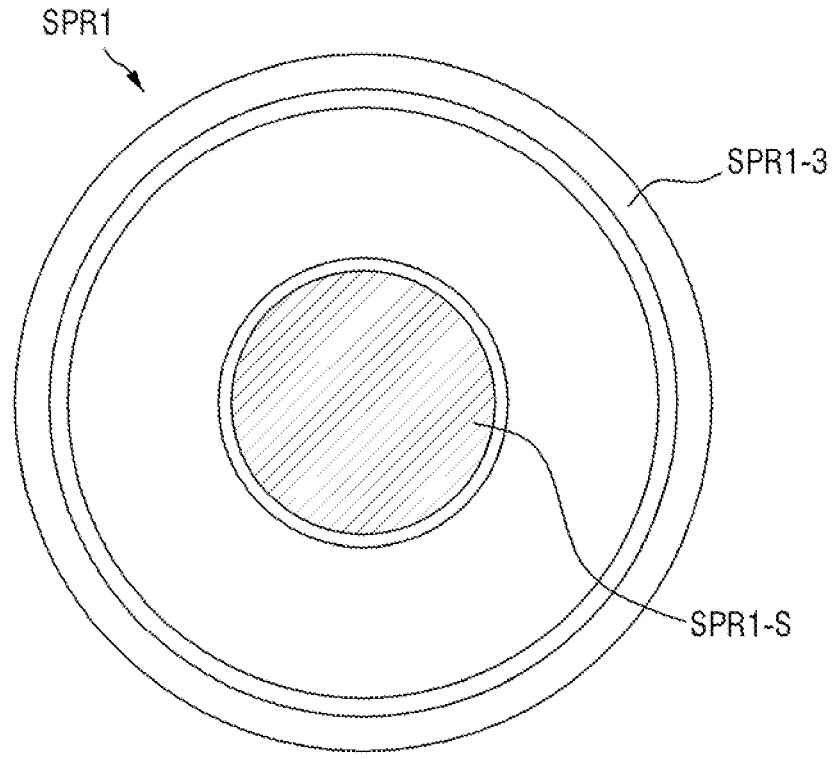
FIG. 12 is a plan view of a sprayer according to an embodiment.

FIG. 9 is a perspective view of a sprayer according to an embodiment, and FIG. 10 is an exploded perspective view of the sprayer according to an embodiment. FIG. 11 is a plan view of a sprayer according to an embodiment, and FIG. 12 is a plan view of a sprayer according to an embodiment.

Referring to FIGS. 9 and 11, in an embodiment, first sprayer SPR1 directly sprays droplets towards an object. The droplets have an average size that ranges, for example, from about microns to greater than 100 microns, or from about 35 microns to about 55 microns, but are not necessarily limited thereto.

The first sprayer SPR1 may include a container body SPR1-1 that accommodates the contrast medium, an injector SPR1-2, and a funnel-type nozzle SPR1-3.

The container body SPR1-1 includes an inner container SPR1-10 and an upper cap SPR1-12.

The inner container SPR1-10 has an accommodation space SPR1-10s formed therein, and a bottleneck portion SPR1-101 formed at an upper portion thereof. The bottleneck SPR1-101 is provided with a screw thread SPR1-101a on an outer circumferential surface.

The upper cap SPR1-12 has a screw thread SPR1-121a formed on an inner circumferential surface of a sidewall SPR1-121 thereof, and can be screwed onto the container body SPR1-1.

In addition, a gasket SPR1-13 is disposed between the upper cap SPR1-12 and an upper end of the inner container SPR1-10.

The upper cap SPR1-12 includes an upward bent portion SPR1-123a in which a bottom surface SPR1-123 connected to an upper end of the sidewall SPR1-121 is upwardly bent, a horizontal portion SPR1-123b that extends from an upper end of the upward bent portion SPR1-123a in a central direction, and a downward bent portion SPR1-123c that is downwardly bent from an end of the horizontal portion SPR1-123b, such that a fitting space SPR1-123d is formed between the upward bent portion SPR1-123a and the downward bent portion SPR1-123c.

The container body SPR1-1 includes a spray plate SPR1-11 that is detachably attached to an inlet of the inner container.

The spray plate SPR1-11 includes one or more openings SPRH. The contrast medium of the container body SPR1-1 passes through the openings SPRH to form the droplets.

The injector SPR1-2 includes an inner pipe body SPR1-21 formed as a pipe that has a hollow interior, a piston valve SPR1-22, a piston SPR1-23, and a spring SPR1-24.

The inner pipe body SPR1-21 has the form of a pipe that has a hollow interior, and includes an upper coupling portion SPR1-211, a body portion SPR1-212, and a lower coupling portion SPR1-213.

An upper end of a wall surface of the upper coupling portion SPR1-211 fits into the fitting space SPR1-123d and coupled thereto.

A fine projection protrudes outwardly on an upper end of the upper coupling portion SPR1-211 and a groove large enough to fit the projection is formed in the fitting space SPR1-123d, such that the projection fits into the groove by force fitting and is fixed thereto.

The body portion SPR1-212 has inner and outer diameters smaller than those of the upper coupling portion SPR1-211 while being integrally connected with the upper coupling portion SPR1-211 to form an upper inner step SPR1-212a and an upper outer step SPR1-212b between the upper coupling portion SPR1-211 and the body portion SPR1-212.

The lower coupling portion SPR1-213 has inner and outer diameters smaller than those of the body portion SPR1-212 while being integrally connected with the body portion SPR1-212 to form a lower inner step SPR1-213a and a lower outer step SPR1-213b between body portion SPR1-212 and the lower coupling portion SPR1-213.

The piston valve SPR1-22 is closed at the top and open at the bottom as illustrated, and has a lower wall surface inserted into the inner space of the body portion SPR1-212 to be vertically movable.

In addition, the piston valve SPR1-22 includes a protruding rib SPR1-221 that protrudes outwardly and from a middle wall surface of the piston valve SPR1-22 to upwardly be inclined, and a lower wall surface of the protruding rib SPR1-221 is formed with a spring pressing portion SPR1-222 having an outer diameter smaller than that of an upper portion.

The spring SPR1-24 is installed inside the body portion SPR1-212 while an upper end thereof is supported by the spring pressing portion SPR1-222 and a lower end thereof is supported by the lower inner step SPR1-213a to allow the piston valve SPR1-22 to have upward elasticity.

The piston SPR1-23 has the form of a pipe that has a hollow interior as illustrated. A lower portion of the piston SPR1-23 is inserted into the upper coupling portion SPR1-211, whose outer diameter gradually increases, and a pressurizing portion SPR1-231 that presses the upper portion of the piston valve SPR1-22 is formed inside the piston SPR1-23.

The funnel-type nozzle SPR1-3 includes a liquid discharge passage SPR1-24 that is coupled to and communicates with an upper portion of the piston SPR1-23, and the nozzle SPR1-3 is detachably coupled at the end of the liquid discharge passages SPR1-24 to the upper portion of the piston SPR1-23.

When the injector SPR1-2 receives an electric signal, the piston SPR1-23 positioned at an inlet of the injector SPR1-2 operates, and an inlet of the piston SPR1-23 opens. Thereafter, the contrast medium is moved, sprayed, and discharged out of the injector SPR1-2 by pressure maintained inside the injector SPR1-2.

The funnel-type nozzle SPR1-3 is disposed at an inlet of the container body SPR1-1 provided with the spray plate SPR1-11. The funnel-type nozzle SPR1-3 includes a pipe portion SPR1-31 and a funnel portion SPR1-32.

The pipe portion SPR1-31 is detachably coupled to the container body SPR1-1. The pipe portion SPR1-31 is coupled to the upward bent portion SPR1-123a of the upper cap SPR1-12 so that the pipe portion SPR1-31 fits into the upward bent portion SPR1-123a of the upper cap SPR1-12.

The funnel portion SPR1-32 includes a first end SPR1-32a that has a smaller opening and a second end SPR1-32b that has a larger opening than the first end SPR1-32a. The funnel portion SPR1-32 has a diameter that gradually increases from the first end SPR1-32a to the second end SPR1-32b. A diameter SPRD1 of the opening of the first end SPR1-32a of the funnel portion SPR1-32 is less than a diameter of the first lens hole LSH1, and a diameter SPRD2 of the opening of the second end SPR1-32b is greater than the diameter of the first lens hole LSH1. For example, the diameter SPRD2 of the opening of the second end SPR1-32b of the funnel portion SPR1-32 is equal to or less than about 1 to 2 mm, and the diameter of the first lens hole LSH1 is equal to or less than about 1 mm.

Figure 15A:
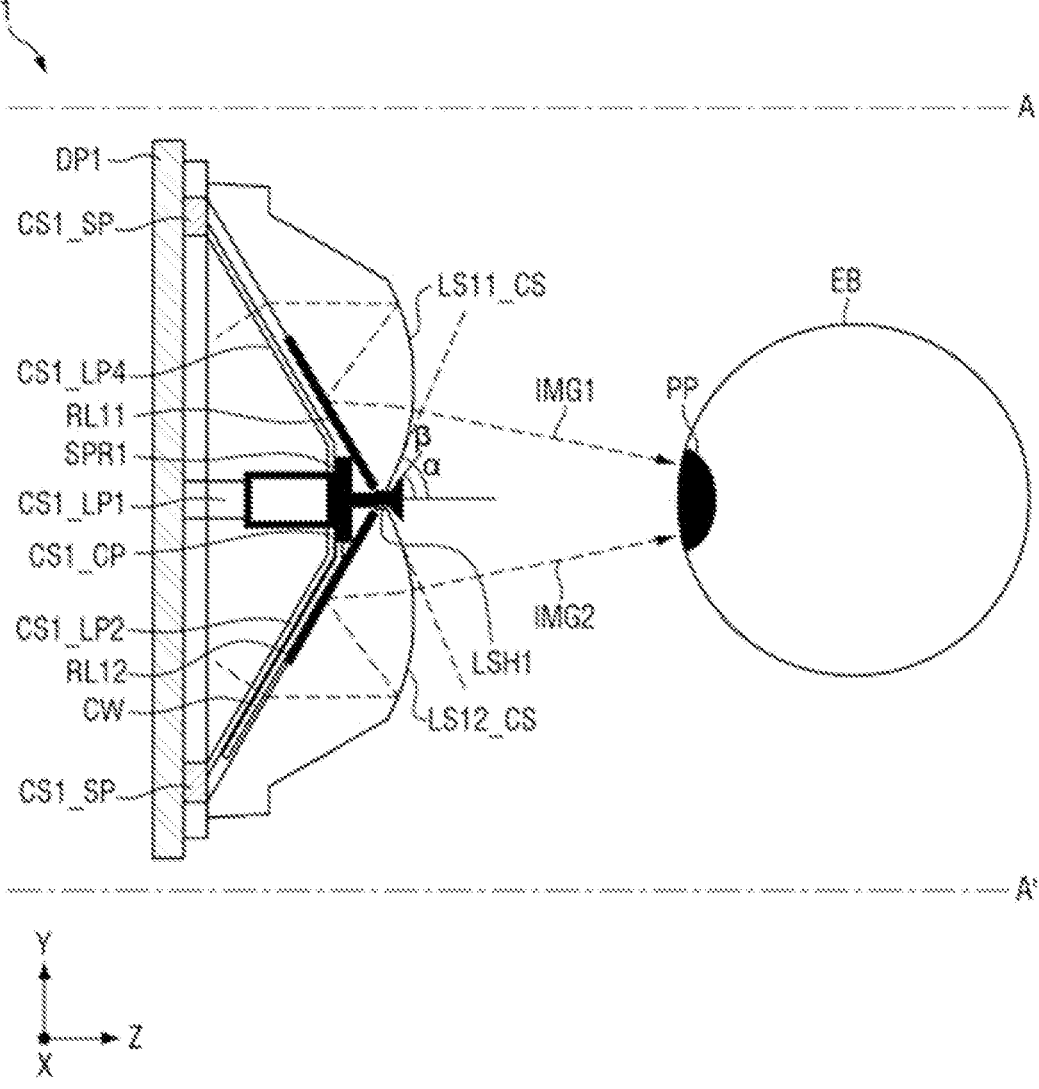
FIGS. 15A to 15C are cross-sectional views taken along line A-A' of FIG. 6.
Figure 15B:
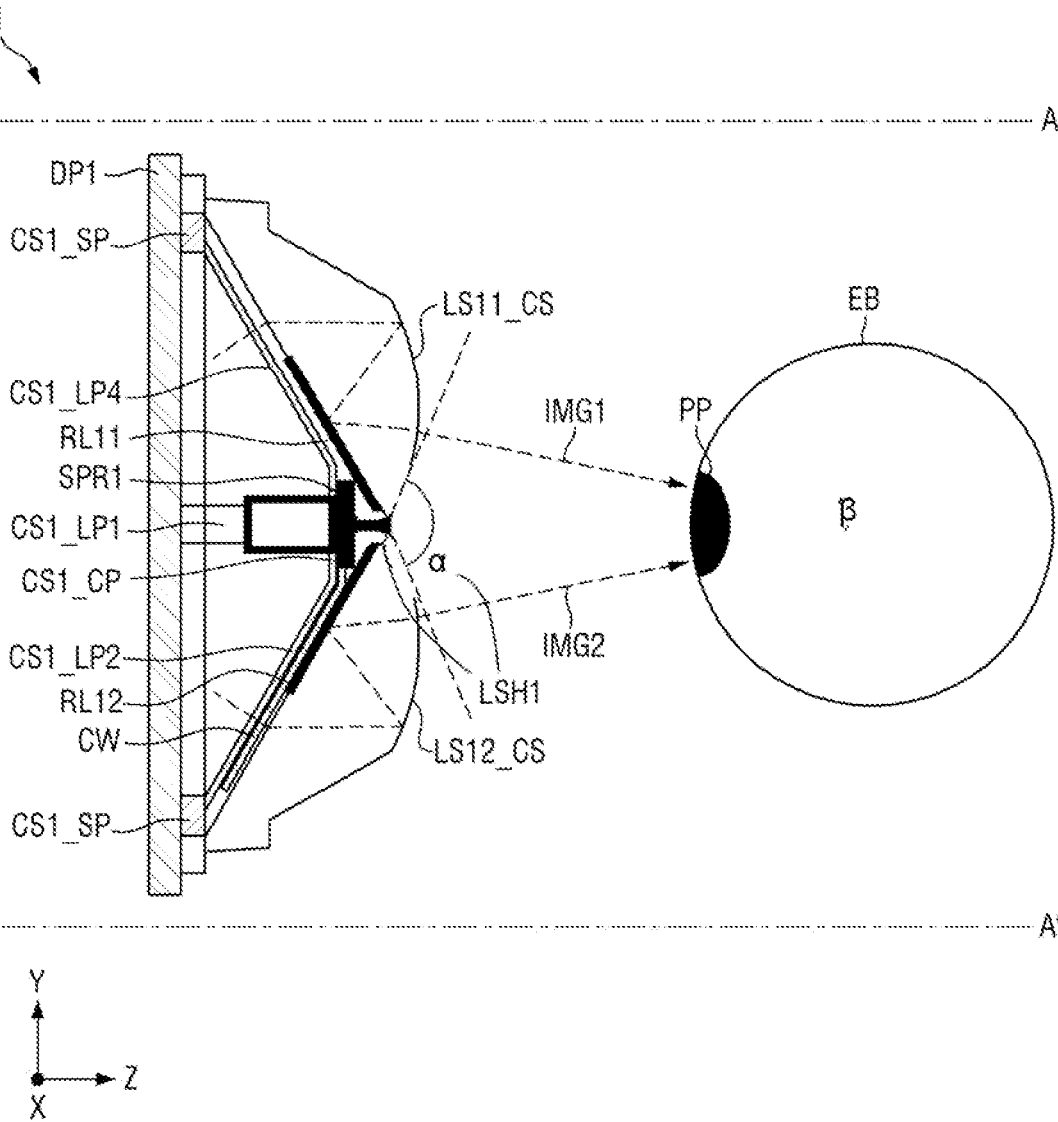

The funnel portion SPR1-32 is disposed inside the first lens hole LSH1, and as illustrated in FIG. 15A to be described below, when the contrast medium is discharged, the funnel portion SPR1-32 protrudes out from the first multi-channel lens LS1 in the third direction Z through the first lens hole LSH1. When the discharging of the contrast medium is finished, the funnel-type nozzle SPR1-3 is retracted back into the first lens hole LSH1 as illustrated in FIG. 15B to be described below. Since a diameter of an outer opening of the funnel-type nozzle SPR1-3 is greater than the diameter of the first lens hole LSH1, the funnel-type nozzle SPR1-3 can be formed of an elastic material so that a ripple is formed in the funnel portion SPR1-32 when the funnel portion SPR1-32 retracts into the first lens hole LSH1, and the ripple disappears when funnel portion SPR1-32 protrudes outward from the first lens hole LSH1. The number and shape of the ripples may differ depending on the material and thickness of the funnel portion SPR1-32.

In an embodiment, referring to FIG. 15A to be described below, an angle α of a taper of the funnel portion SPR1-32 with respect to a side surface of the pipe portion SPR1-31 is about 10° to 30°. The angle α of the taper of the funnel portion SPR1-32 is 2 to 3 times smaller than an angle β of the outer surface of the first sub-lens LS11. The angle β of the outer surface of the first sub-lens LS11 is the largest of the angles between a central axis passing through the center of the first lens hole LSH1 and a tangent to the lens LS11. In an embodiment, referring to FIG. 15A to be described below, the angle β of the outer surface of the first sub-lens LS11 is about 10° to 60°

Referring to FIGS. 11 and 12, in an embodiment, the sprayer SPR1 further includes a shutter SPR1-S. The shutter SPR1-S overlaps the spray plate SPR1-11 and covers the entire spray plate SPR1-11. The shutter SPR1-S is disposed outside the spray plate SPR1-11. When the shutter SPR1-S is closed, the contrast medium inside the first sprayer SPR1 cannot be discharged.

When the injector, SPR1-2 in FIG. 9, receives an electrical signal, the pistol, SPR1-23 in FIG. 10, and the shutter SPR1-S positioned at the inlet of the injector operate, and inlets of the shutter SPR1-S and the piston SPR1-23 open. Thereafter, the contrast medium is moved, sprayed, and discharged out of the injector SPR1-2 by a pressure maintained inside the injector SPR1-2.

Accordingly, the contrast medium is prevented from contaminating the inside of the first multi-channel lens LS1 through the first lens hole LSH1.

Figure 13:
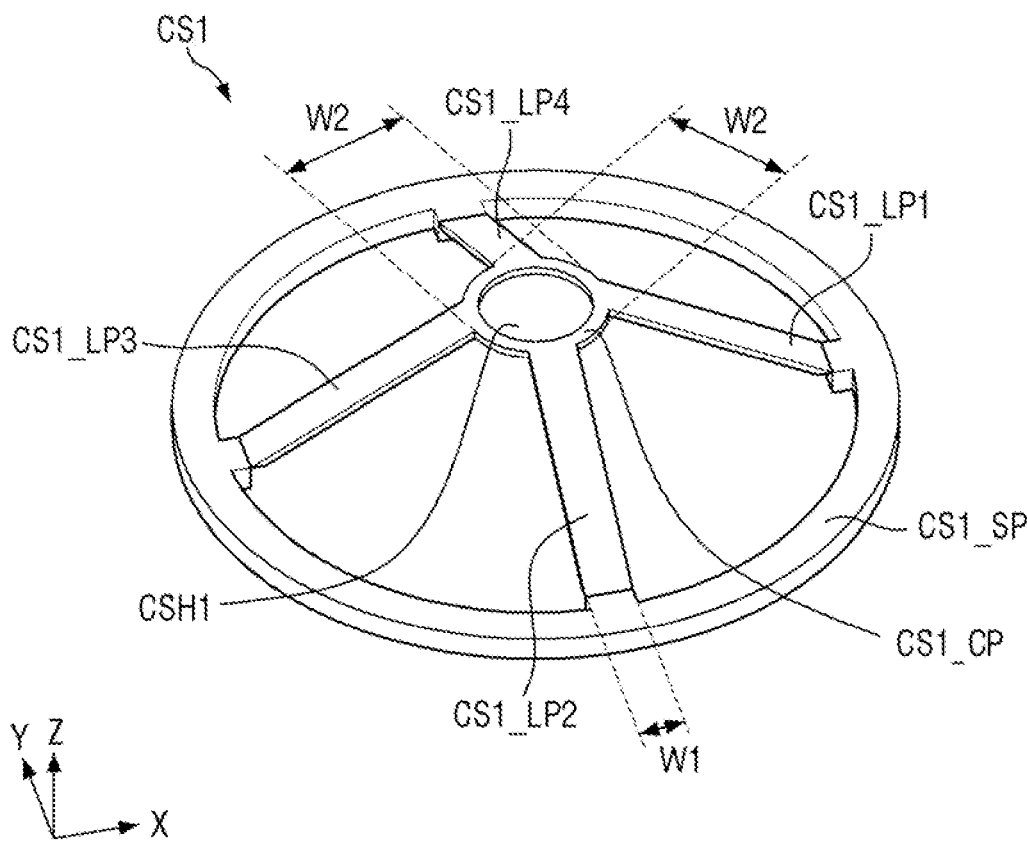
FIG. 13 is a perspective view of a holding member according to an embodiment.
Figure 14:
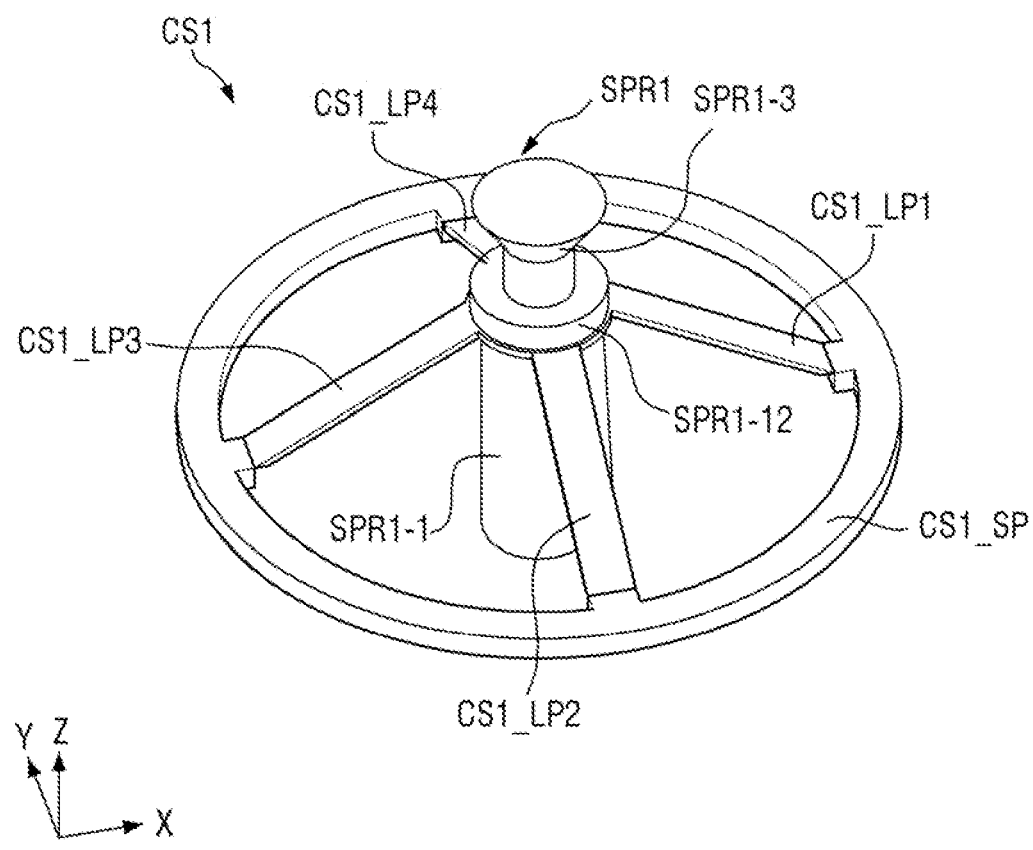
FIG. 14 is a perspective view of a holding member on which a sprayer is held, according to an embodiment.

FIG. 13 is a perspective view of a holding member according to an embodiment, and FIG. 14 is a perspective view of a holding member on which a sprayer is held, according to an embodiment.

Referring to FIGS. 4, 5, 7, 8, 13 and 14, the first holding member CS1 includes a support ring CS1_SP, a plurality of leg portions CS1_LP1, CS1_LP2, CS1_LP3, and CS1_LP4, and a sprayer holding portion CS1_CP.

In an embodiment, the support ring CS1_SP, the plurality of leg portions CS1_LP1, CS1_LP2, CS1_LP3, and CS1_LP4, and the sprayer holding portion CS1_CP are integrally formed. For example, the support ring CS1_SP, the plurality of leg portions CS1_LP1, CS1_LP2, CS1_LP3, and CS1_LP4, and the sprayer holding portion CS1_CP refer to a specific portion or a specific area of the first holding member CS1. However, embodiments of the present disclosure are not necessarily limited thereto, and in an embodiment, the support ring CS1_SP, the plurality of leg portions CS1_LP1, CS1_LP2, CS1_LP3, and CS1_LP4, and the sprayer holding portion CS1_CP are separate members that are distinct from each other.

The support ring CS1_SP is connected to the plurality of leg portions CS1_LP1, CS1_LP2, CS1_LP3, and CS1_LP4, and supports the plurality of leg portions CS1_LP1, CS1_LP2, CS1_LP3, and CS1_LP4. In an embodiment, the support ring CS1_SP is a ring-shaped member that corresponds to a shape of an edge of the first multi-channel lens LS1, and the edge of the first multi-channel lens LS1 is held and supported on the support ring CS1_SP. However, embodiments of the present disclosure are not necessarily limited thereto, and in some embodiments, the support ring CS1_SP has various other planar shapes that support the plurality of leg portions CS1_LP1, CS1_LP2, CS1_LP3, CS1_LP4 and the first multi-channel lens LS1, such as a rectangle, a square, or an oval. In some embodiments, the support ring CS1_SP is replaced with a plurality of members for each of the plurality of leg portions CS1_LP1, CS1_LP2, CS1_LP3, and CS1_LP4 that support each of the plurality of leg portions CS1_LP1, CS1_LP2, CS1_LP3, and CS1_LP4.

The plurality of leg portions CS1_LP1, CS1_LP2, CS1_LP3, and CS1_LP4 are disposed inside the support ring CS1_SP. One side of each of the plurality of leg portions CS1_LP1, CS1_LP2, CS1_LP3, and CS1_LP4 is connected to the support ring CS1_SP, and the other side of each of the plurality of leg portions CS1_LP1, CS1_LP2, CS1_LP3, and CS1_LP4 is connected to the sprayer holding portion CS1_CP. The plurality of leg portions CS1_LP1, CS1_LP2, CS1_LP3, and CS1_LP4 are inclined with respect to the third direction Z. The other side of each of the plurality of leg portions CS1_LP1, CS1_LP2, CS1_LP3, and CS1_LP4 and the sprayer holding portion CS1_CP connected thereto protrude further in the third direction Z than the support ring CS1_SP.

The sprayer holding portion CS1_CP is disposed inside the support ring CS1_SP and supports the first sprayer SPR1. The sprayer holding portion CS1_CP overlaps the center of the first multi-channel lens LS1. The sprayer holding portion CS1_CP is supported by the plurality of leg portions CS1_LP1, CS1_LP2, CS1_LP3, and CS1_LP4.

Referring further to FIG. 8, the support ring CS1_SP, the plurality of leg portions CS1_LP1, CS1_LP2, CS1_LP3, and CS1_LP4, and the sprayer holding portion CS1_CP overlap edge portions of the plurality of sub-lenses LS11, LS12, LS13, LS14, LS21, LS22, LS23, and LS24 in a plan view and transmit most of the light passing through the plurality of sub-lenses LS11, LS12, LS13, LS14, LS21, LS22, LS23, and LS24 without being visually recognized by a user. Light passing through a central portion of each of the plurality of sub-lenses LS11, LS12, LS13, LS14, LS21, LS22, LS23, and LS24 is incident on a user's pupil, and light passing through the edge portions of the plurality of sub-lenses LS11, LS12, LS13, LS14, LS21, LS22, LS23, and LS24 is blocked or refracted so as not to be incident on the user's pupil.

The plurality of leg portions CS1_LP1, CS1_LP2, CS1_LP3, and CS1_LP4 overlap the plurality of lens boundaries in the third direction Z, respectively. Since light passing through the plurality of lens boundaries is not incident on the user's eyeball due to refraction by the plurality of sub-lenses LS11, LS12, LS13, LS14, LS21, LS22, LS23, and LS24, the plurality of leg portions CS1_LP1, CS1_LP2, CS1_LP3, and CS1_LP4 are not visually recognized by the user. The plurality of lens boundaries refer to a specific portion or a specific area adjacent to the edge of each sub-lens and in which the light that passes through the multi-channel lenses is not visually recognized by the user due to the refraction of light by the multi-channel lenses.

A plurality of spaces are formed between the plurality of leg portions CS1_LP1, CS1_LP2, CS1_LP3, and CS1_LP4 so that the light passing through each of the sub-lenses is not blocked. As illustrated in FIG. 8, each of the plurality of spaces overlaps the central portions of the plurality of sub-lenses LS11, LS12, LS13, LS14, LS21, LS22, LS23, and LS24, and areas of the plurality of leg portions CS1_LP1, CS1_LP2, CS1_LP3, and CS1_LP4 are smaller than areas of the plurality of spaces between the plurality of leg portions CS1_LP1, CS1_LP2, CS1_LP3, and CS1_LP4 in a plan view.

The number of the plurality of leg portions CS1_LP1, CS1_LP2, CS1_LP3, and CS1_LP4 corresponds to the number of sub-lenses (channels) of the first multi-channel lens LS1. The number of the plurality of leg portions CS1_LP1, CS1_LP2, CS1_LP3, and CS1_LP4 is less than or equal to the number of sub-lenses (channels) of the first multi-channel lens LS1. The number of the plurality of leg portions CS1_LP1, CS1_LP2, CS1_LP3, and CS1_LP4 is less than or equal to the number of boundaries between sub-lenses of the first multi-channel lens LS1. For example, when the first multi-channel lens LS1 has n sub-lenses, the first holding member CS1 has n or fewer leg portions. In an embodiment, the first multi-channel lens LS1 has four sub-lenses (channels), and the first holding member CS1 has four leg portions, but embodiments of the present disclosure are not necessarily limited thereto.

The sprayer holding portion CS1_CP includes a first leg portion CS1_LP1 that overlaps the first lens boundary BD1, a second leg portion CS1_LP2 that overlaps the second lens boundary BD2, a third leg portion CS1_LP3 that overlaps the third lens boundary BD3, and a fourth leg portion CS1_LP4 that overlaps the fourth lens boundary BD4.

The sprayer holding portion CS1_CP and the first sprayer SPR1 overlap the lens hole LSH1 of the first multi-channel lens LS1 in the third direction Z.

Referring further to FIG. 13, in an embodiment, each of the plurality of leg portions CS1_LP1, CS1_LP2, CS1_LP3, and CS1_LP4 has a first width W1 that is sufficiently small so as not to be visually recognized by the user. The first width W1 is measured in a direction intersecting or perpendicular to an extension direction from the support ring CS1_SP of each leg portion toward the sprayer holding portion CS1_CP.

For example, the first width W1 is equal to or less than about 3.0 mm. For example, a diameter of the first multi-channel lens LS1 is about 30 mm to 60 mm. For another example, the first width W1 is about 1/13 to 1/20 of the diameter of the first multi-channel lens LS1 in a plan view. However, the size of the first width W1 is not necessarily limited thereto, and can vary according to a design of the display device 1.

The sprayer holding portion CS1_CP has a circular shape in a plan view. However, the shape of the sprayer holding portion CS1_CP is not necessarily limited thereto, and the sprayer holding portion CS1_CP may have various other planar shapes, such as a rectangle, a square, a rhombus, an oval, or a trapezoid. The sprayer holding portion CS1_CP has a second width W2 greater than the first width W1 in a plan view.

The second width W2 is measured in a diagonal direction that intersects the first direction X and the second direction Y. The second width W2 is measured from the boundary between the first leg portion CS1_LP1 and the second leg portion CS1_LP2 to the boundary between the third leg portion CS1_LP3 and the fourth leg portion CS1_LP4, is measured from the boundary between the second leg portion CS1_LP2 and the third leg portion CS1_LP3 to the boundary between the first leg portion CS1_LP1 and the fourth leg portion CS1_LP4. The second width W2 is equal to or greater than a width of the first sprayer SPR1.

The sprayer holding portion CS1_CP includes a holding hole CSH1 in a central portion thereof.

The holding hole CSH1 has a greater diameter than the first lens hole LSH1. For example, the diameter of the holding hole CSH1 is about 6.0 mm to 10 mm, and the diameter of the first lens hole LSH1 is about 1.0 mm to 2.0 mm. For another example, the diameter of the holding hole CSH is about 3 to 5 times the diameter of the first lens hole LSH1. However, the size of the diameter of the first lens hole LSH1 and the size of the diameter of the holding hole CSH are not necessarily limited thereto, and can vary according to a design of the display device 1.

As illustrated in FIG. 14, in an embodiment, the diameter of the holding hole CSH1 is equal to or greater than a diameter of the inner container SPR1-1 of the first sprayer SPR1. The inner container SPR1-1 of the first sprayer SPR1 is accommodated in the holding hole CSH1.

The upper cap SPR1-12 disposed on the bottleneck portion of the inner container SPR1-1 has a larger diameter than the holding hole CSH1. Accordingly, the holding hole CSH1 supports the upper cap SPR1-12 of the inner container SPR1-1. For example, the diameter of the holding hole CSH1 is greater than the diameter of the inner container SPR1-1 by 1 mm and less than the diameter of the upper cap SPR1-12 of the inner container SPR1-1 by 1 mm, but is not necessarily limited thereto, and can vary depending on a design of the display device 1.

In an embodiment, a fitting groove is formed in the upper cap SPR1-12 of the inner container SPR1-1, and a fitting protrusion is formed on an outer circumferential surface of the holding hole CSH. The fitting groove and the fitting protrusion can be fastened.

Referring to FIG. 5, in an embodiment, the second holding member CS2 also includes a support ring CS2_SP, a plurality of leg portions CS2_LP1, CS2_LP2, CS2_LP3, and CS2_LP4, and a sprayer holding portion CS2_CP, like the first holding member CS1.

The support ring CS2_SP, the plurality of leg portions CS2_LP1, CS2_LP2, CS2_LP3, and CS2_LP4, the sprayer holding portion CS2_CP, and the second sprayer SPR2 of the second holding member CS2 have substantially the same or similar structure as the support ring CS1_SP, the plurality of leg portions CS2_LP1, CS2_LP2, CS2_LP3, and CS2_LP4, the sprayer holding portion CS2_CP, and the first sprayer SPR1 of the first holding member CS1.

The plurality of leg portions CS2_LP1, CS2_LP2, CS2_LP3, and CS2_LP4 of the second holding member CS2 overlap the plurality of lens boundaries of the second multi-channel lens LS2, respectively. The plurality of leg portions CS2_LP1, CS2_LP2, CS2_LP3, and CS2_LP4 of the second holding member CS2 include a fifth leg portion CS2_LP1, a sixth leg portion CS2_LP2, a seventh leg portion CS2_LP3, and an eighth leg portion CS2_LP4 that overlap the fifth lens boundary BD5, the sixth lens boundary BD6, the seventh lens boundary BD7, and the eighth lens boundary BD8, respectively. The fifth leg portion CS2_LP1, the sixth leg portion CS2_LP2, the seventh leg portion CS2_LP3, and the eighth leg portion CS2_LP4 have substantially the same or similar width as the first leg portion CS1_LP1, the second leg portion CS1_LP2, the third leg portion CS1_LP3, and the fourth leg portion CS1_LP4, respectively, and thus are not visually recognized by the user.

Similarly, the support ring CS2_SP and the sprayer holding portion CS2_CP of the second holding member CS2 also overlap an edge portion of the second multi-channel lens LS2 and the center of the second multi-channel lens LS2, respectively, so as not to be visually recognized by the user.

Figure 15C:
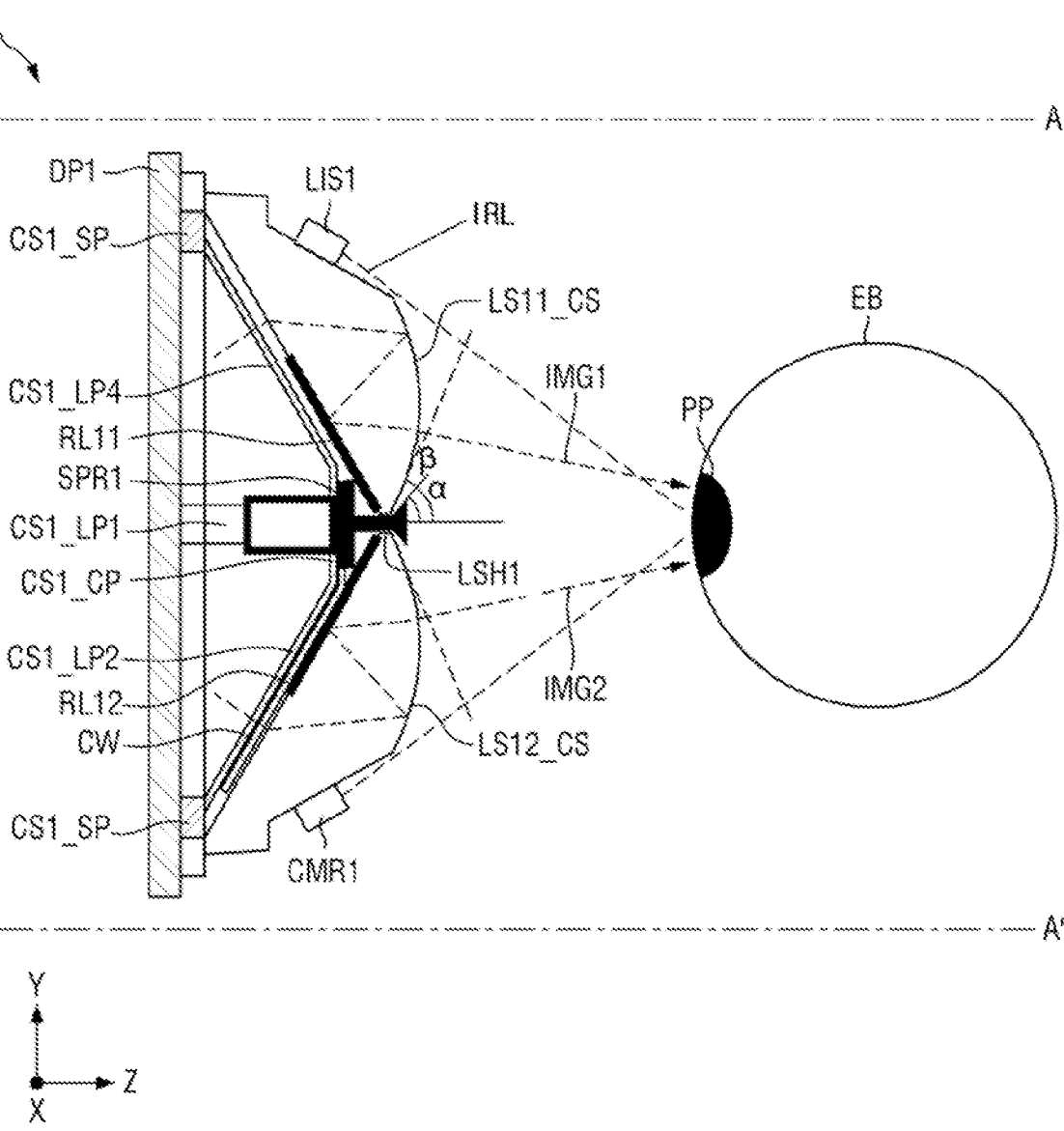

FIGS. 15A to 15C are cross-sectional views taken along line A-A' of FIG. 6. FIG. 15A is a cross-sectional view taken along line A-A' at the time of discharging the contrast medium, and FIG. 15B is a cross-sectional view taken along line A-A' before and after the contrast medium is discharged.

Referring to FIGS. 6 to 15A and 15B, in an embodiment, the first multi-channel lens LS1 includes a rear surface that faces the first display member DP1 and the first holding member CS1 and that has a concave shape. The rear surface of each of the plurality of sub-lenses LS11, LS12, LS13, and LS14 in the first multi-channel lens LS1 forms the rear surface of the first multi-channel lens LS1. The rear surface of the first multi-channel lens LS1 is opposite to the eyepiece surfaces, namely the second outer surface LS11_CS, the fourth outer surface LS12_CS, the sixth outer surface LS13_CS, and the eighth outer surface LS14_CS.

The first multi-channel lens LS1 includes reflective lenses RL11, RL12, RL13, and RL14 disposed on respective rear surfaces of the plurality of sub-lenses LS11, LS12, LS13, and LS14. The reflective lenses RL11, RL12, RL13, and RL14 reflect light reflected from the sub-lenses LS11, LS12, LS13, LS14, LS21, LS22, LS23, and LS24.

The reflective lenses RL11, RL12, RL13, and RL14 are disposed on the rear surfaces of the sub-lenses LS11, LS12, LS13, and LS14. A first reflective lens RL11 is disposed on the rear surface of the first sub-lens LS11, a second reflective lens RL12 is disposed on the rear surface of the second sub-lens LS12, a third reflective lens RL13 is disposed on the rear surface of the third sub-lens LS13, and a fourth reflective lens RL14 is disposed on the rear surface of the fourth sub-lens LS14.

A concave inner space that has an approximate triangular shape that protrudes toward the first lens hole LSH1 at the center of the first multi-channel lens LS1 is formed between the rear surface of the first multi-channel lens LS1 and the support ring CS1_SP of the first holding member CS1 in a cross-sectional view. The plurality of leg portions CS1_LP1, CS1_LP2, CS1_LP3, and CS1_LP4 and the sprayer holding portion CS1_CP are accommodated in the inner space.

The plurality of reflective lenses RL11, RL12, RL13, and RL14 overlap the first sprayer SPR1 in the third direction Z. The third direction Z is a direction in which the user's eyeball is positioned.

In an embodiment, the first to fourth reflective lenses RL11, RL12, RL13, and RL14 cover the first sprayer SPR1. Fifth to eighth reflective lenses RL21, RL22, RL23, and RL24 cover the second sprayer SPR2. The sprayer holding portions CS1_CP and CS2_CP and the sprayers SPR1 and SPR2 are not visually recognized by the user due to the first to fourth reflective lenses RL11, RL12, RL13, and RL14.

The first to fourth reflective lenses RL11, RL12, RL13, and RL14 change a path of light reflected in an eyeball direction from the first multi-channel lens LS1. The fifth to eighth reflective lenses RL21, RL22, RL23, and RL24 change a path of light reflected in an eyeball direction from the second multi-channel lens LS2.

As described above, the plurality of leg portions CS1_LP1, CS1_LP2, CS1_LP3, and CS1_LP4 of the first multi-channel lens LS1 protrude from the support ring CS1_SP in the third direction Z. Each of the leg portions CS1_LP1, CS1_LP2, CS1_LP3, and CS1_LP4 is spaced apart from the first multi-channel lens LS1 by a predetermined interval. None of the leg portions CS1_LP1, CS1_LP2, CS1_LP3, and CS1_LP4 is in direct contact with the first multi-channel lens LS1. However, embodiments of the present disclosure are not necessarily limited thereto, and in an embodiment, the plurality of leg portions CS1_LP1, CS1_LP2, CS1_LP3, and CS1_LP4 are in contact with the first multi-channel lens LS1.

As illustrated in FIG. 14, in an embodiment, the second leg portion CS1_LP2 and the fourth leg portion CS1_LP4 are spaced apart from the rear surface of the first multi-channel lens LS1 by a predetermined interval in the third direction Z. In addition, the first leg portion CS1_LP1 and the third leg portion CS1_LP3 are also spaced apart from the rear surface of the first multi-channel lens LS1 by a predetermined interval in the third direction Z. For example, each of the first leg portion CS1_LP1, the second leg portion CS1_LP2, the third leg portion CS1_LP3, and the fourth leg portion CS1_LP4 is spaced apart from the first multi-channel lens LS1 by about 1.0 mm, but embodiments of the present disclosure are not necessarily limited thereto.

The holding hole CSH1 of the sprayer holding portion CS1_CP overlaps the first lens hole LSH1 of the first multi-channel lens LS1 in the third direction Z in a cross-sectional view.

Since the rear surface of the first multi-channel lens LS1 has a concave shape, a concave inner space is formed between the first multi-channel lens LS1 and the first display member DP1 in which the first sprayer SPR1 is held in the holding hole CSHs of the sprayer holding portion CS1_CP.

The first sprayer SPR1 overlaps the center of the first multi-channel lens LS1 in the third direction Z, and is accommodated in the concave space between the sprayer holding portion CS1_CP and the rear surface of the first multi-channel lens LS1.

The sprayer holding portion CS1_CP forms a space in which the first sprayer SPR1 is accommodated between the center of the first multi-channel lens LS1 and a portion adjacent thereto, and the sprayer holding portion CS1_CP.

The sprayer holding portion CS1_CP is spaced apart from the rear surface of the first multi-channel lens LS1 in the third direction Z in a cross-sectional view. The interval in the third direction Z between the sprayer holding portion CS1_CP and the rear surface of the first multi-channel lens LS1 increases toward the edge where the first outer surface LS11_NS, third outer surface LS12_NS, fifth outer surface LS13_NS and seventh outer surface LS14_NS meet the second outer surface LS11_CS, the fourth outer surface LS12_CS, the sixth outer surface LS13_NS, and the eighth outer surface LS14_CS, respectively, and decreases toward the center of the first multi-channel lens LS1. The interval in the third direction Z between the sprayer holding portion CS1_CP and the rear surface of the first multi-channel lens LS1 has a maximum value at the edge portions of the first multi-channel lens LS1 where the first outer surface LS11_NS, third outer surface LS12_NS, fifth outer surface LS13_NS and seventh outer surface LS14_NS meet the second outer surface LS11_CS, the fourth outer surface LS12_CS, the sixth outer surface LS13_NS, and the eighth outer surface LS14_CS, respectively. For example, a maximum interval between the sprayer holding portion CS1_CP and the rear surface of the first multi-channel lens LS1 is about 5.0 mm, but is not necessarily limited thereto. As described above, the plurality of sub-lenses LS11, LS12, LS13, and LS14 respectively provide the plurality of channels through which the light emitted from the first display member DP1 or the second display member DP2 passes. Each of the sub-lenses magnifies light emitted from a specific area of the first display member DP1 or the second display member DP2 to have the same magnification or to have different magnifications. The light that passes through each of the sub-lenses includes a partial image for implementing one complete VR video, and the light is focused on the user's pupil to provide the user with a complete VR video.

For example, as illustrated in FIGS. 15A and 15B, in an embodiment, light emitted from different areas of the first display member DP1 passes through the first multi-channel lens LS1 through different paths. The first sub-lens LS11 provides a channel through which light IMG1 emitted from one area, such as an upper end of the first display member DP1, passes through the second outer surface LS11_CS, and the second sub-lens LS12 provides a channel through which light IMG2 emitted from another area, such as a lower end of the first display member DP1, passes through the fourth outer surface LS12_CS. One area of the first display member DP1 at least partially overlaps the first sub-lens LS11 in the third direction Z, and the other area of the second display member DP2 at least partially overlaps the second sub-lens LS12 in the third direction Z. Likewise, the third sub-lens LS13 and the fourth sub-lens LS14 also provide channels through which the light emitted from a specific area of the first display member DP1 passes, respectively. In an embodiment, the light that passes through each of the sub-lenses LS11, LS12, LS13, and LS14 is provided to the user through two refractions and two reflections, but is not necessarily limited thereto.

Referring to FIG. 15C, in an embodiment, the first wavelength light source LIS1 that emits light of a first wavelength in response to the contrast medium is integrally formed with the first wavelength camera sensor CMR1.

The contrast medium is sprayed into the user's eyeball from the first sprayer SPR1. The contrast medium is a fluorescein solution. The fluorescein solution dyes the tear layer of the cornea, making it easy to observe changes in the tear layer.

The first wavelength light source LIS1 emits light of a first wavelength. The first wavelength light increases a transmittance of the contrast medium. The first wavelength is in a range of 430 nm to 480 nm.

The first wavelength light IRL is reflected from the user's tear film and is incident on the first wavelength camera sensor CMR1. The first wavelength camera sensor CMR1 includes an image sensor. The first wavelength camera sensor CMR1 generates a first image or a first video of the user's tear film by receiving the light emitted from the first wavelength light source LIS1 and reflected from the user's tear film. The first wavelength camera sensor CMR1 measures a tear film breakage time of the user by analyzing the first image or the first video. The tear film breakage time refers to a time in the first video from when the contrast medium is sprayed by the first sprayer SPR1 until the tear film is broken and a change in luminance starts to appear.

In some embodiments, as the first wavelength light source LIS1 is integrally built into the first wavelength camera sensor CMR1, an overall volume of the display device 1 is reduced, so that a compact display device 1 can be realized.

Referring to FIGS. 15A and 15B, in an embodiment, the display device 1 further include a connection wiring CW that connects the injector of the first sprayer SPR1 and the processor.

The connection wiring CW is disposed on the first holding member CS1. The connection wiring CW is disposed between the first holding member CS1 and the first multi-channel lens LS1 in a cross-sectional view. The connection wiring CW is disposed on the sprayer holding portion CS1_CP and at least one of the plurality of leg portions CS1_LP1, CS1_LP2, CS1_LP3, and CS1_LP4. For example, as illustrated in FIG. 15A, the connection wiring CW is disposed on the second leg portion CS1_LP2, but embodiments are not necessarily limited thereto. In some embodiments, the connection wiring CW is also disposed on one of the first leg portion CS1_LP1, the third leg portion CS1_LP3, or the fourth leg portion CS1_LP4.

The connection wiring CW is disposed on a surface of the sprayer holding portion CS1_CP that faces the first multi-channel lens LS1 and one surface of at least one of the plurality of leg portions CS1_LP1, CS1_LP2, CS1_LP3, and CS1_LP4. In some embodiments, the connection wiring CW is disposed on an other surface of the sprayer holding portion CS1_CP that faces the first display member DP1 and an other surface of at least one of the plurality of leg portions CS1_LP1, CS1_LP2, CS1_LP3, and CS1_LP4. The other surface of the sprayer holding portion CS1_CP and the other surface of at least one of the plurality of leg portions CS1_LP1, CS1_LP2, CS1_LP3, CS1_LP4 is opposite to the surface of the sprayer holding portion CS1_CP and opposite to the surface of at least one of the plurality of leg portions CS1_LP1, CS1_LP2, CS1_LP3, and CS1_LP4 that face the first multi-channel lens LS1.

As described above, since the second multi-channel lens LS2, the second holding member CS2, and the second sprayer SPR2 are substantially the same as or similar to the first multi-channel lens LS1, the first holding member CS1, and the first sprayer SPR1, repeated descriptions thereof will be omitted below.

FIG. 15C is a cross-sectional view of a display device 1 in which the first wavelength light source LIS1 that emits first wavelength light IRL toward the user's cornea is disposed on an outer surface of the first multi-channel lens LS1 of FIGS. 15A and 15B.

Referring to FIGS. 6, 7, and 15C, in an embodiment, the first wavelength light source LIS1 is disposed on the outer surface of the first multi-channel lens LS1, but is not disposed on the second outer surface LS11_CS, the fourth outer surface LS12_CS, the sixth outer surface LS13_CS, or the eighth outer surface LS14_CS. Accordingly, the light that passes through the second outer surface LS11_CS, the fourth outer surface LS12_CS, the sixth outer surface LS13_CS, and the eighth outer surface LS14_CS is not blocked and a user's gaze is not obstructed.

Figure 16:
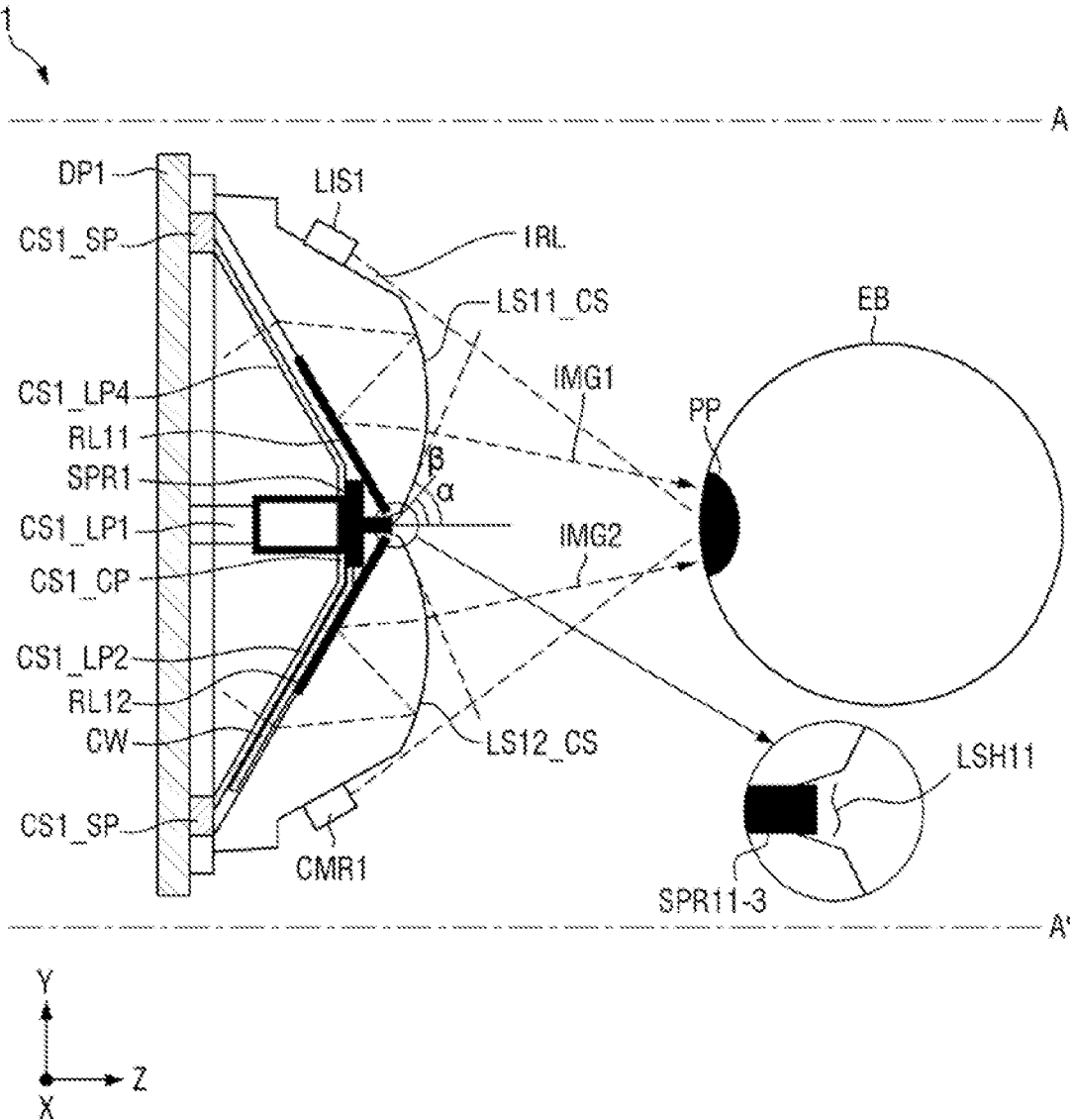
FIG. 16 is a cross-sectional view taken along line A-A' of FIG. 6, according to another embodiment.

FIG. 16 is a cross-sectional view taken along line A-A' of FIG. 6 according to an embodiment.

Referring to FIG. 16, in an embodiment, a nozzle SPR11-3 of the sprayer SPR1 is a pipe-type nozzle rather than a funnel type. When a pipe-type nozzle is adopted, one end of the nozzle SPR11-3 is in contact with the first lens hole LSH1, and the first lens hole LSH1 has a tapered inclination like the funnel portion SPR1-32. For example, referring to an enlarged view of the first lens hole LSH1, the first lens hole LSH1 has a larger diameter from one end to the other end. One end of the first lens hole LSH1 is disposed closer to the first display member DP1 than the other end.

In such a modified example, the first lens hole LSH1 controls an angle of spraying of the contrast medium, instead of the funnel-type nozzle. For example, to prevent the sprayed contrast medium from flowing inside, an outer circumference of the nozzle SPR11-3 is in close contact with an inner side of the first lens hole LSH1.

Figure 17:
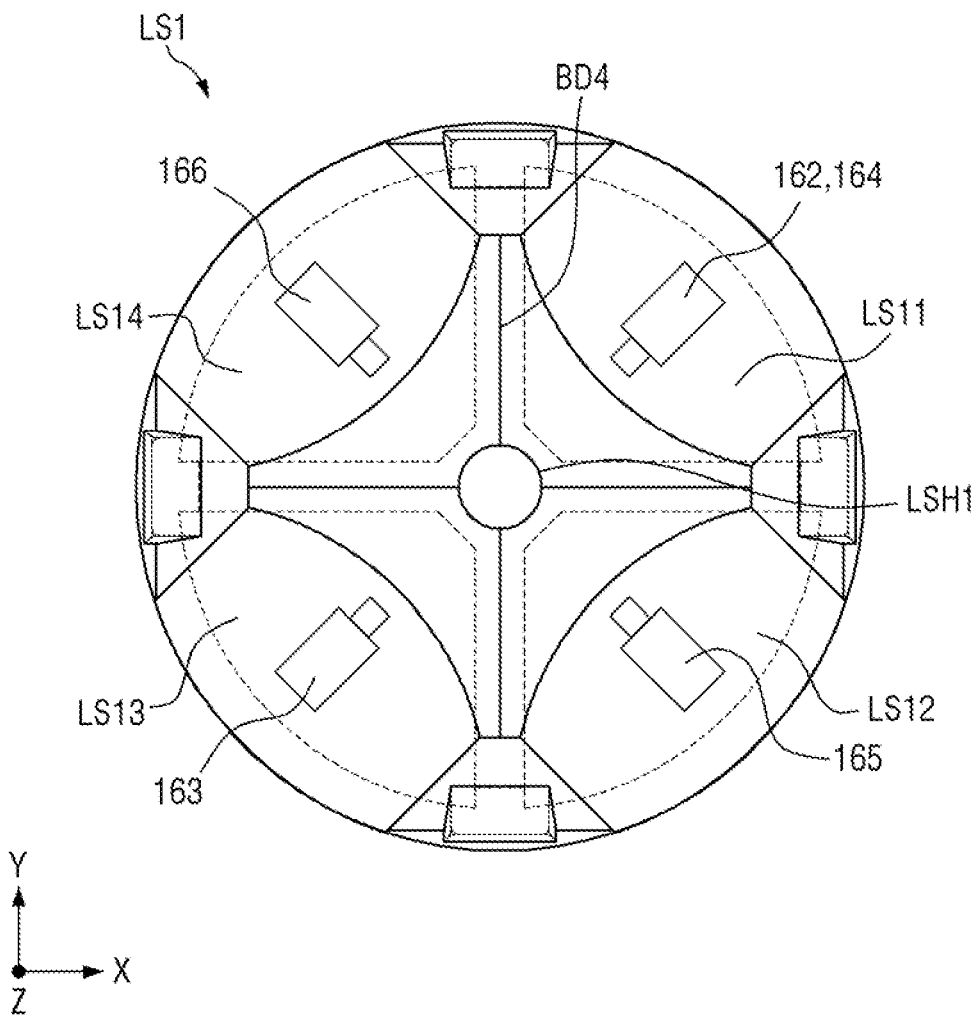
FIG. 17 is a plan view of a first multi-channel lens according to an embodiment.

FIG. 17 is a plan view of a first multi-channel lens according to an embodiment.

Referring to FIG. 17, in an embodiment, a first wavelength light source 162, a first wavelength camera sensor 163, a second wavelength light source 164 and a second wavelength camera sensor 165 are disposed on an outer surface of the multi-channel lens LS1. The first wavelength light source 162 emits light of a first wavelength, and the first wavelength camera sensor 163 generates a first video by receiving the first wavelength light emitted from the first wavelength light source 162 and reflected from the user's eyeball and measures a tear film breakage time of the user based on the first video. The second wavelength light source 164 emits light of a second wavelength, and a second wavelength camera sensor 165 generates a second video by receiving the second wavelength light emitted from the second wavelength light source 164 and reflected from the user's eyeball and detects the number of eye blinks for a preset period based on the second video. The first wavelength light source 162 and the second wavelength light source 164 may be integrally formed, but embodiments are not necessarily limited thereto. The first wavelength light source 162 and the second wavelength light source 164 are disposed on the outer surface of the first sub-lens LS11. The first wavelength camera sensor 163 is disposed on the outer surface of the third sub-lens LS13. The second wavelength camera sensor 165 is disposed on the outer surface of the second sub-lens LS12. A temperature sensor 166 is disposed on the outer surface of the fourth sub-lens LS14. However, embodiments of the present disclosure are not necessarily limited thereto, and one or more of the first wavelength light source 162, the first wavelength camera sensor 163, the second wavelength light source 164, and the second wavelength camera sensor 165 may be disposed on the outer surfaces of different sub-lenses. The first wavelength light source 162, the first wavelength camera sensor 163, the second wavelength light source 164, the second wavelength camera sensor 165, and the temperature sensor 166 correspond to the first wavelength light source 162, the first wavelength camera sensor 163, the second wavelength light source 164, the second wavelength camera sensor 165, and the temperature sensor 166 of FIGS. 1-3.

Since the first wavelength light source 162, the first wavelength camera sensor 163, the second wavelength light source 164, and the second wavelength camera sensor 165 on the outer surface of the second multi-channel lens LS2 are substantially the same as or similar to those shown in FIG. 17, repeated descriptions thereof will be omitted below.

Figure 18:
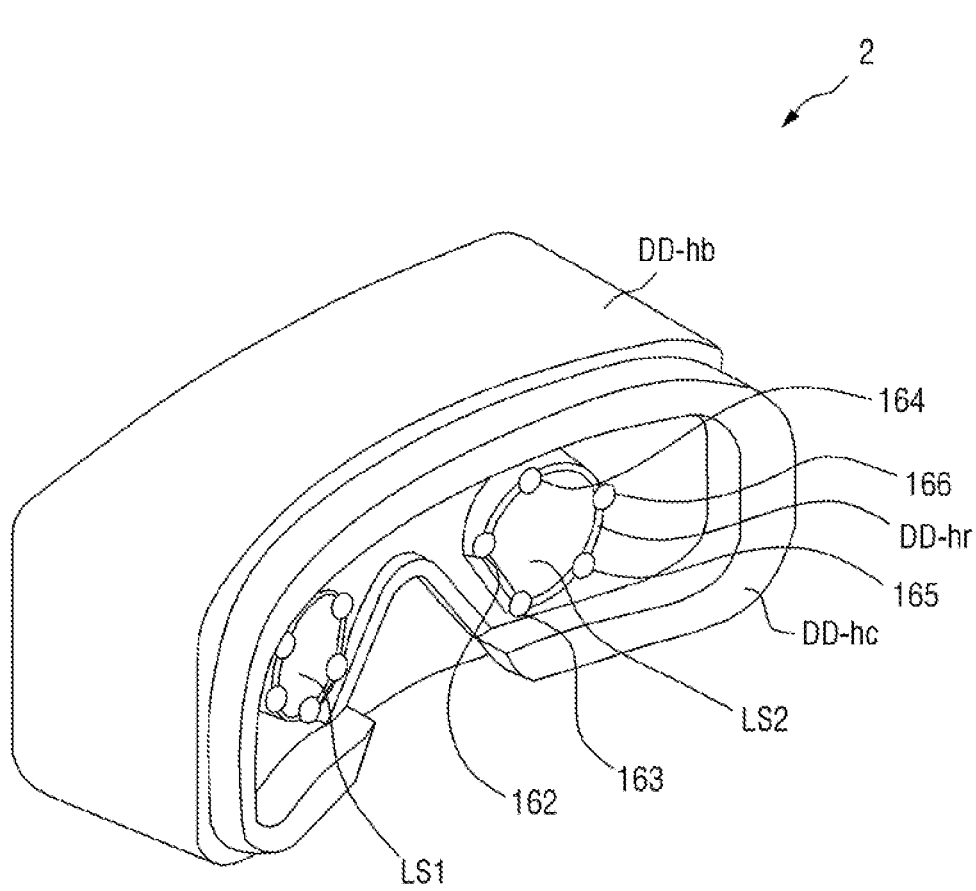
FIG. 18 is a perspective view of a display device according to an embodiment.
Figure 19:
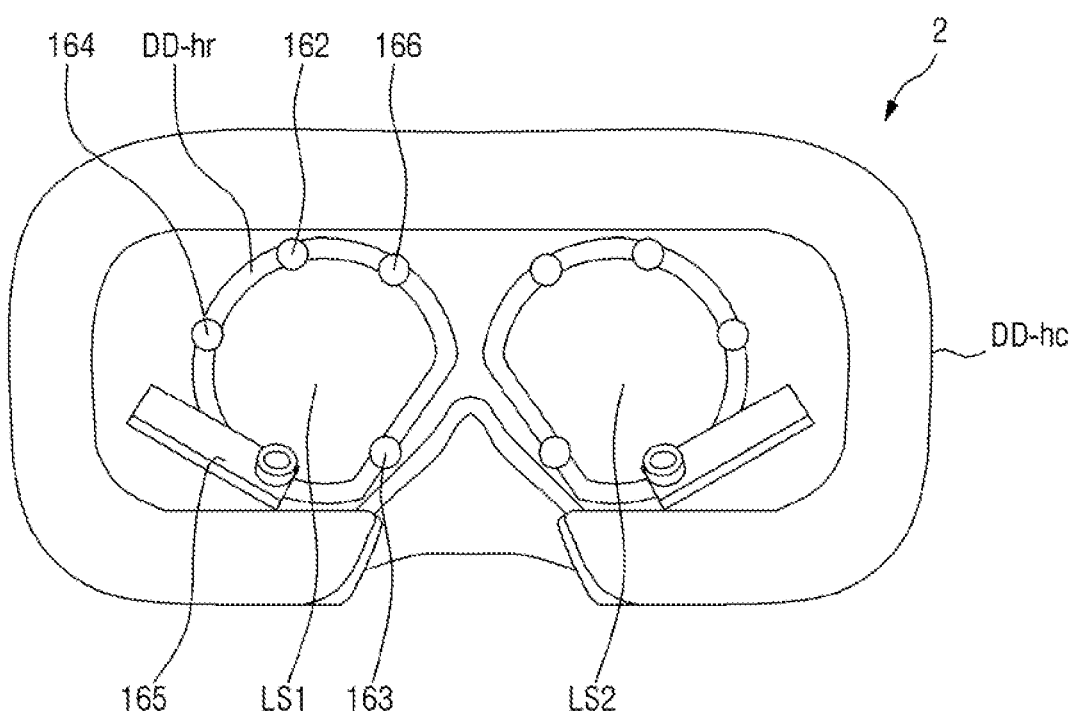
FIG. 19 is a plan view of a display device according to an embodiment.

FIG. 18 is a perspective view of a display device according to an embodiment, and FIG. 19 is a plan view of a display device according to an embodiment.

Referring to FIGS. 18 and 19, in an embodiment, a display device 2 is attachable to and detachable from a face-wearing portion and includes at least most of the components of the display device 1 as described with reference to FIGS. 1 to 17. The display device 2 differs from the display device 1 described with reference to FIGS. 1 to 17 in arrangement positions of the first wavelength light source 162, the first wavelength camera sensor 163, the second wavelength light source 164, the second wavelength camera sensor 165, and the temperature sensor 166.

Before describing the arrangement positions, a structure of a housing DD-h of the display device 2 will be described.

The housing DD-h includes a body portion DD-hb that accommodates the display member (150 in FIG. 1), a face cover portion DD-hc, and a lens rim DD-hr.

The body portion DD-hb forms a basic skeleton of the display device 2, and the display member 150 is coupled thereto or accommodated therein. The shape or type of the body portion DD-hb is also not particularly limited and includes all known in the art.

The face cover portion DD-hc refers to a portion of the housing DD-h that is in close contact with the user's face.

The user views the content provided by the display member 150 by placing the face cover portion DD-hc in close contact with the user's face. For example, in the present specification, the 'face-wearing portion' is a portion of the housing DD-h that is in close contact with the user's pupil. The face cover portion DD-hc is positioned opposite from the display member 150 with respect to the body portion DD-hb, and may extend from the body portion DD-hb or may be detachably disposed on the body part DD-hb.

The face cover portion DD-hc includes a frame made of plastic, such as polyurethane, and the portion of the face cover portion DD-hc that comes in close contact with the user's face is made of sponge or rubber and provides a comfortable fit to the user and prevents slipage, but embodiments of the present disclosure are not necessarily limited thereto.

The lens rim DD-hr surrounds the edges of the first multi-channel lenses LS1 and LS2. The lens rim DD-hr has a shape that corresponds to a planar shape of the first multi-channel lenses LS1 and LS2. For example, when the first multi-channel lenses LS1 and LS2 are approximately circular, the lens rim DD-hr is also approximately circular.

Any pair of the first wavelength light source 162, the first wavelength camera sensor 163, the second wavelength light source 164, the second wavelength camera sensor 165, and the temperature sensor 166 can be disposed around the lens rim DD-hr. Here, the first wavelength camera sensor 163 is a pair, the second wavelength light source 164 and the second wavelength camera sensor 165 are a pair, and the temperature sensor 166 is a pair. The first wavelength light source 162 and the second wavelength light source 164 may also be integrally formed. In addition, the first wavelength light source 162 and the first wavelength camera sensor 163 may also be integrally formed. In addition, the second wavelength light source 164 and the second wavelength camera sensor 165 may also be integrally formed.

In an embodiment described with reference to FIGS. 18 and 19, the first wavelength light source 162, the second wavelength light source 164, the temperature sensor 166, the second wavelength camera sensor 165, and the first wavelength camera sensor 163 are disposed in this order in a clockwise direction, but the arrangement order or direction of each portion is not necessarily limited thereto.

Hereinafter, an operation method of a display device described with reference to FIGS. 1 to 19 will be described.

Figure 20:
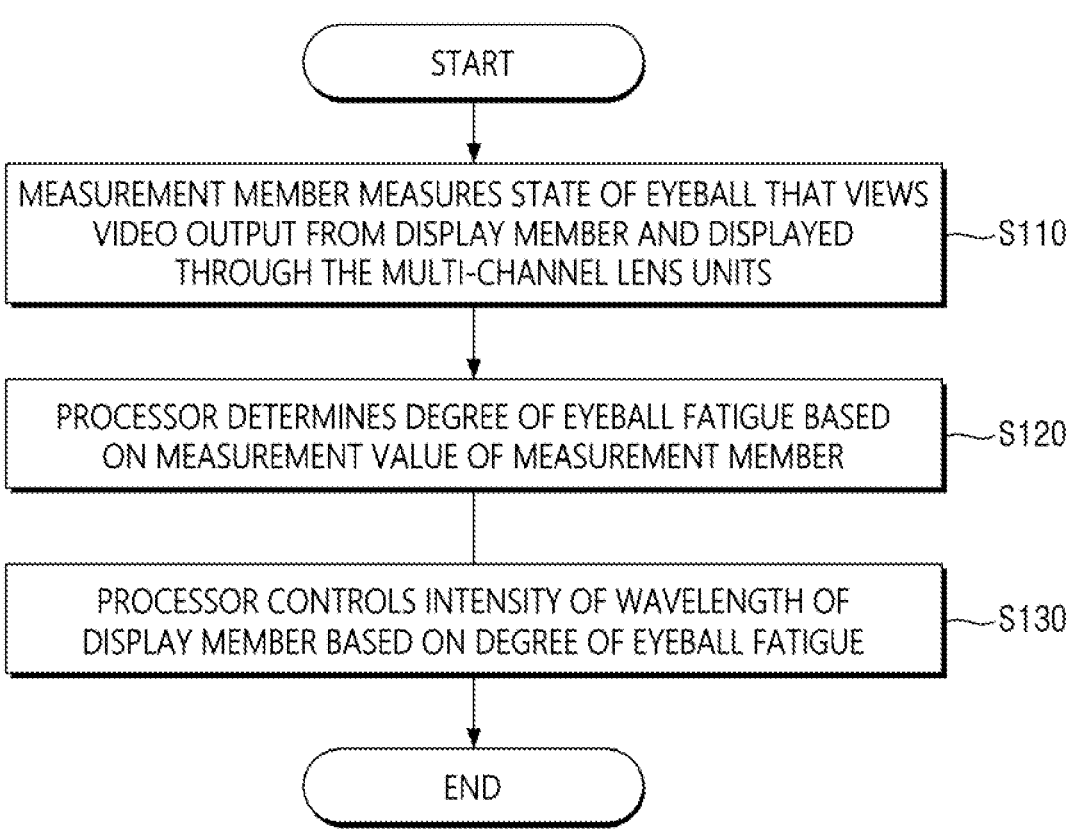
FIG. 20 is a flowchart of an operation method of a display device according to an embodiment.
Figure 21:
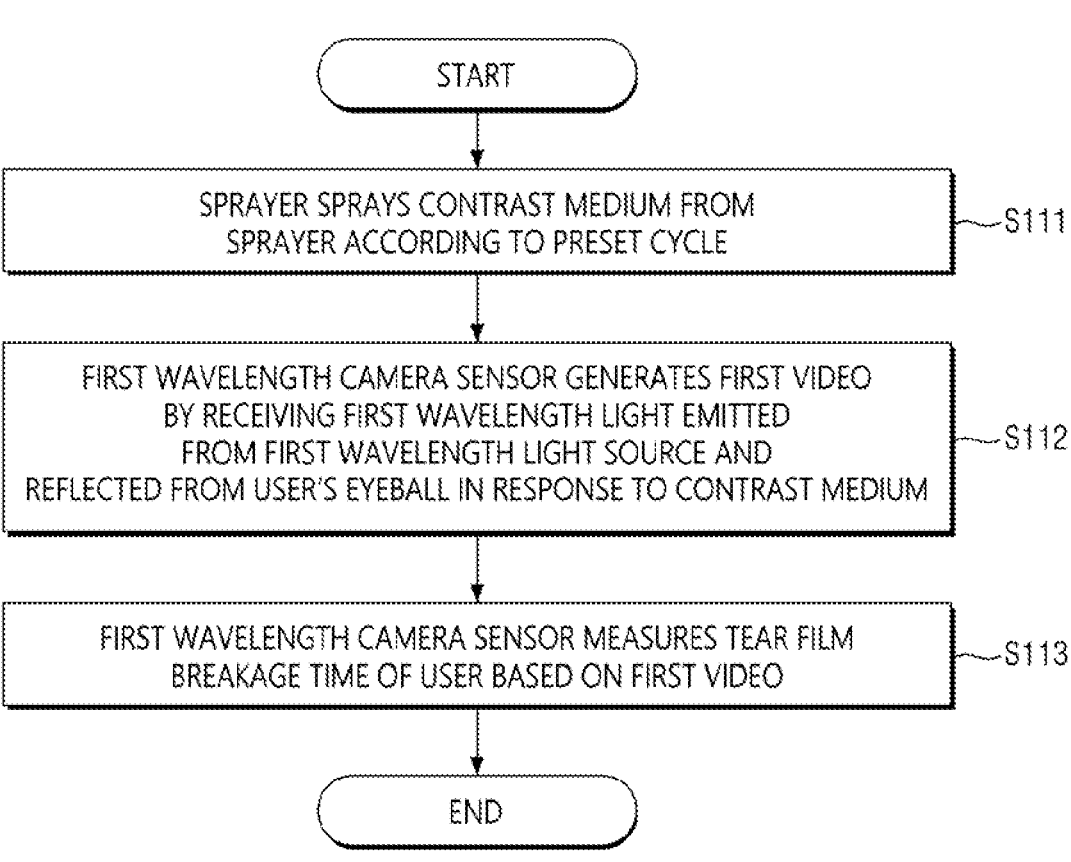
FIG. 21 is a flowchart of step S110 of FIG. 20.
Figure 22:
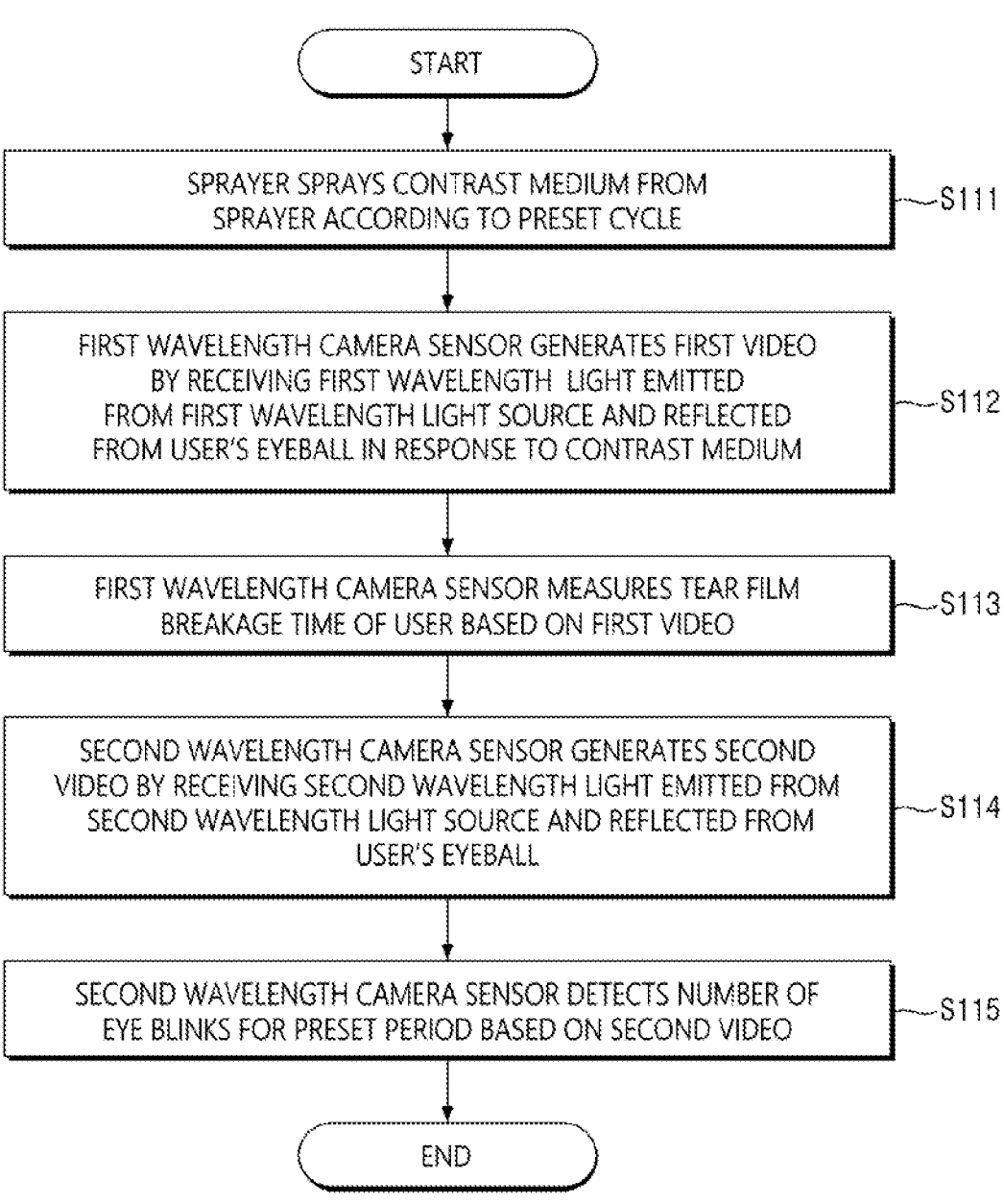
FIG. 22 is a flowchart of another modified example of FIG. 21.
Figure 23:
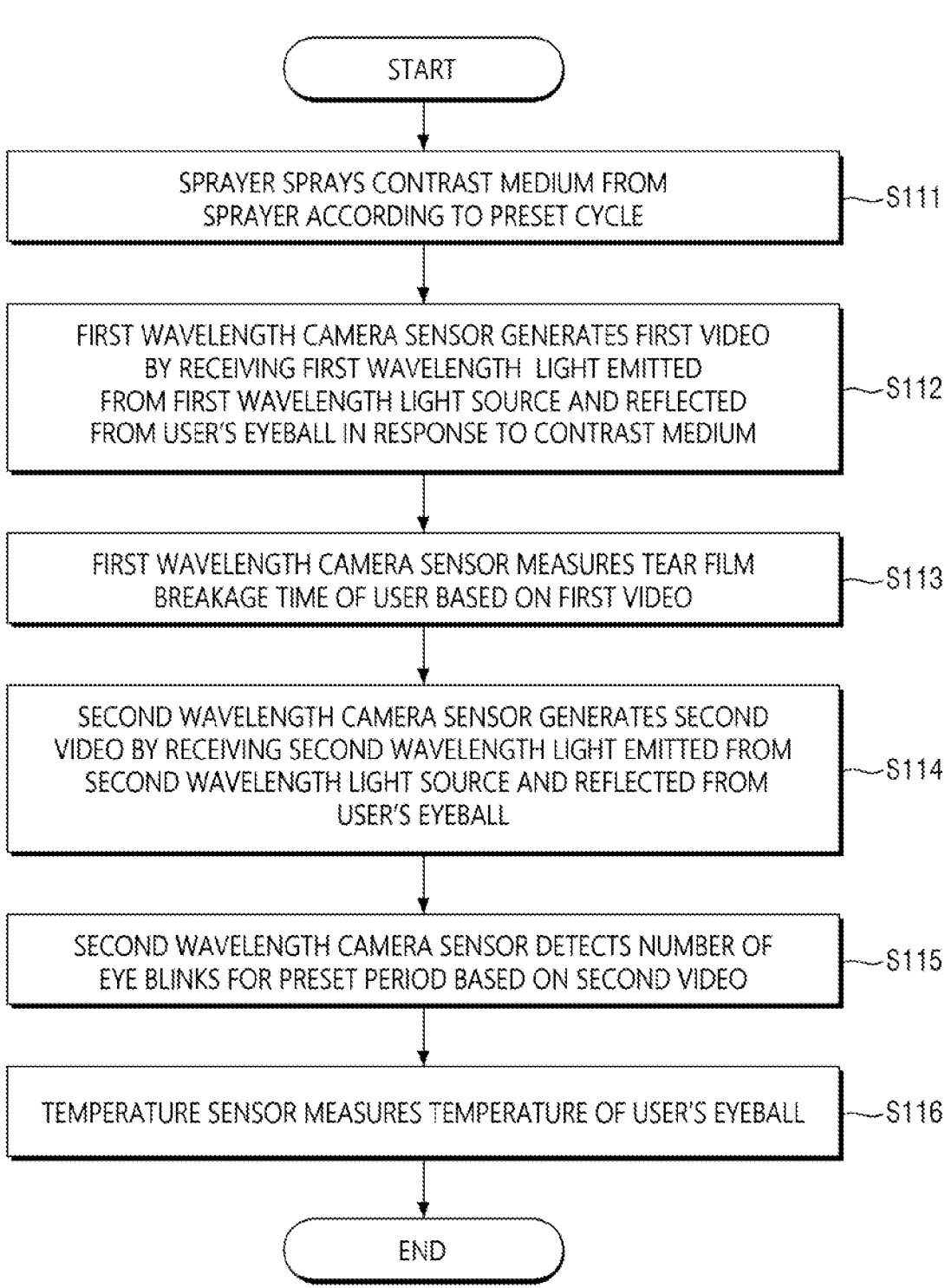
FIGS. 23 and 24 are flowcharts of other modified examples of FIG. 21.
Figure 24:
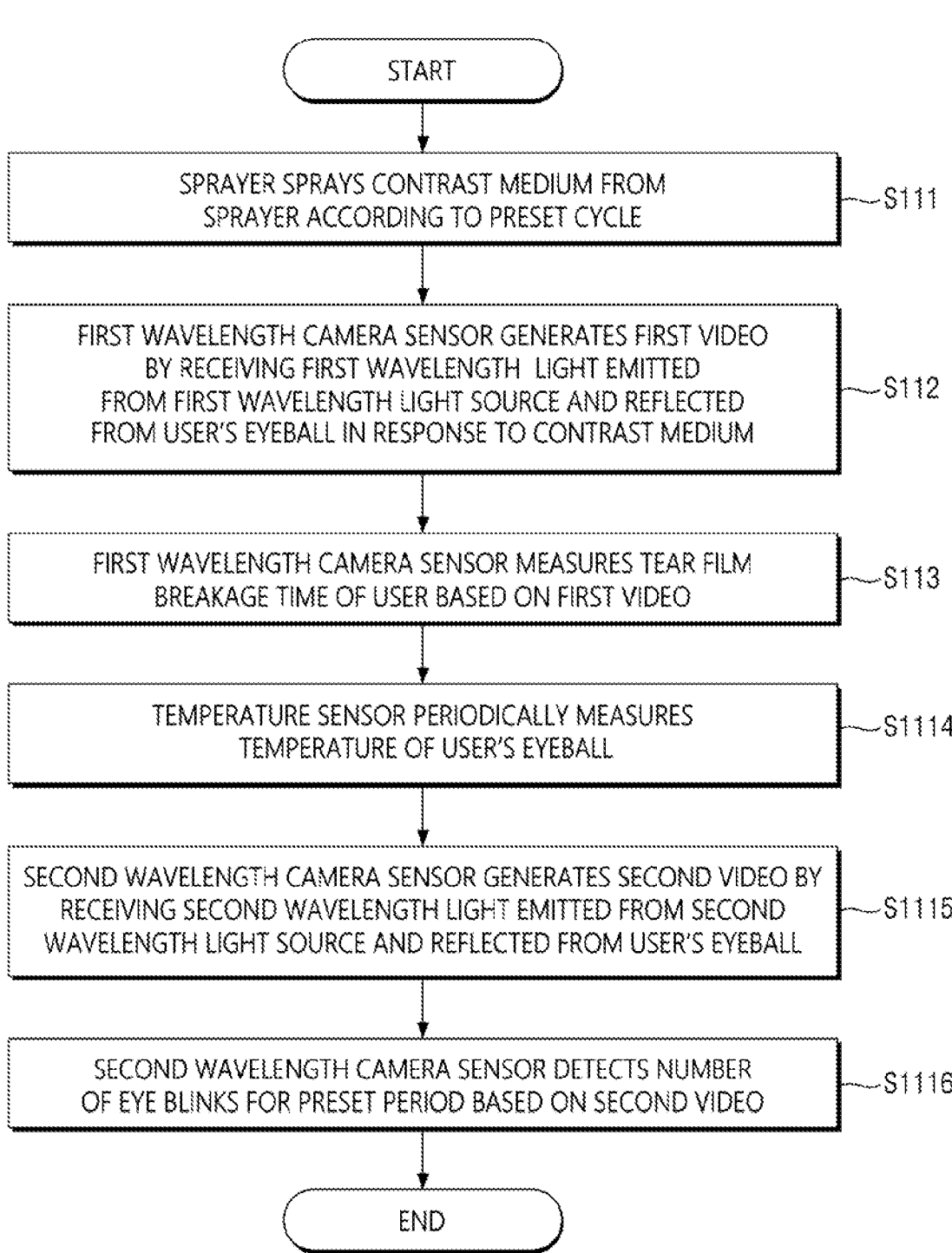
Figure 25:
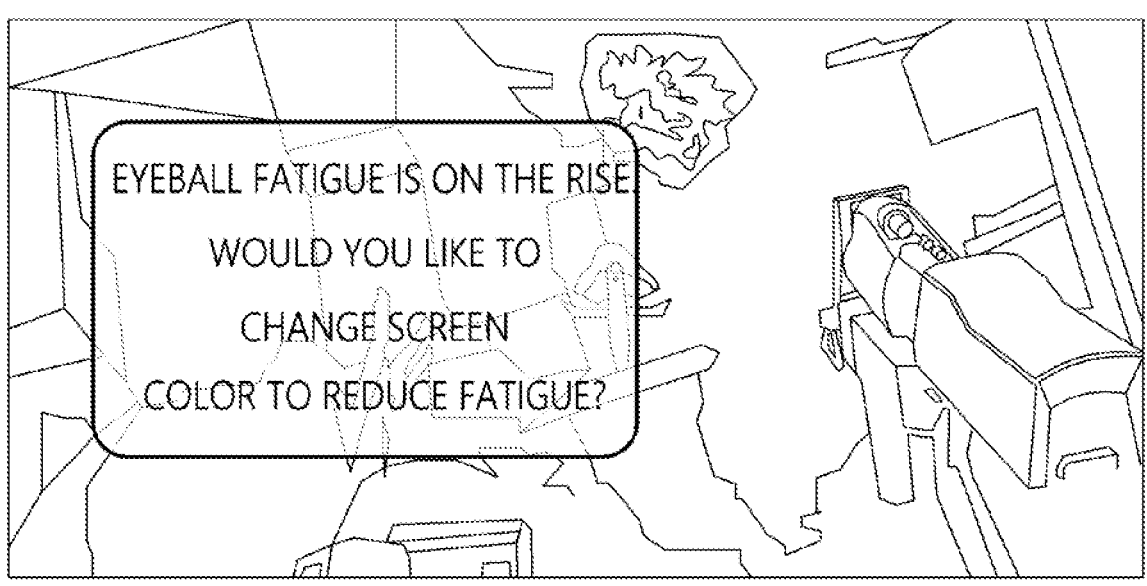
FIG. 25 illustrates a screen that displays an input/output interface according to an embodiment.

FIG. 20 is a flowchart of an operation method of a display device according to an embodiment, FIG. 21 is a flowchart of step S110 of FIG. 20, FIG. 22 is a flowchart of a modified example of FIG. 21, and FIGS. 23 and 24 are flowcharts of another modified example of FIG. 21. FIG. 25 illustrates a screen that displays an input/output interface according to an embodiment.

Referring to FIGS. 20 to 24 and 1 to 3, in an embodiment, in step S110, a measurement member 160 measures a state of an eyeball that views a video output from a display member 150 through multi-channel lens units LS1 and LS2.

In an embodiment, the measurement member 160 includes a sprayer 161, a first wavelength light source 162, and a first wavelength camera sensor 163.

In step S111, the sprayer 161 sprays a contrast medium from the sprayer according to a preset cycle. For example, the cycle is set by a processor 120. The processor 120 shortens the cycle as a viewing time increases.

In step S112, the first wavelength camera sensor 163 generates a first video by receiving a first wavelength light emitted from the first wavelength light source and reflected from a user's eyeball in response to the contrast medium.

In step S113, the first wavelength camera sensor 163 measures a tear film breakage time of the user based on the first video. The tear film breakage time refers to a time in the first video from when the contrast medium is sprayed by the first sprayer SPR1 until the tear film is broken and a change in luminance starts to appear.

In another modified example, a measurement member 260 includes the sprayer 161, the first wavelength light source 162, the first wavelength camera sensor 163, a second wavelength light source 164, and a second wavelength camera sensor 165.

In such a modified example, as illustrated in FIG. 22, steps S114 and S115 are added.

In step S114, the second wavelength camera sensor 165 generates a second video by receiving a second wavelength light emitted from the second wavelength light source and reflected from the user's eyeball.

In step S115, the second wavelength camera sensor 165 detects the number of eye blinks for a preset period based on the second video. For example, an average value of the number of eye blinks per preset period detected for a plurality of times is treated as a detected value of the number of eye blinks.

In another modified example, the measurement member 360 further includes the sprayer 161, the first wavelength light source 162, the first wavelength camera sensor 163, the second wavelength light source 164, the second wavelength camera sensor 165, and a temperature sensor 166.

In such a modified example, as illustrated in FIG. 23, step S116 is added.

In S116, the temperature sensor periodically measure a temperature of the user's eyeball.

The temperature sensor calculates a temperature difference of the eyeball for a preset period based on the measured temperature of the eyeball.

In another modified example, as illustrated in FIG. 24, in step S1114, the temperature sensor periodically measures the temperature of the user's eyeball.

In step S1115, the second wavelength camera sensor 165 generates a second video by receiving second wavelength light emitted from the second wavelength light source and reflected from the user's eyeball.

In step S1116, the second wavelength camera sensor 165 detects the number of eye blinks for a preset period based on the second video. For example, an average value of the number of eye blinks per preset period detected for a plurality of times is treated as a detected value of the number of eye blinks.

In addition, each of the steps is possible in some variations in which the steps occur out of order. For example, each of the steps can be performed substantially simultaneously, or the steps are sometimes performed in a reverse order according to the corresponding function. For example, step 116 can be performed before step S111 or between S113 and S114. Steps S114 and S115 can be performed before step S111. Alternatively, steps S111 and S114 can be simultaneously performed.

In another modified example, the measurement member 160/260/360 includes various modifications of one or more combinations of the sprayer 161, the first wavelength light source 162, the first wavelength camera sensor 163, the second wavelength light source 164, the second wavelength camera sensor 165, and the temperature sensor 166. However, when the measurement member 160/260/360 includes the sprayer 161, the first wavelength light source 162 and the first wavelength camera sensor 163 need to be included together. In addition, when the measurement member 160/260/360 includes the first wavelength light source 162, the first wavelength camera sensor 163 needs to be included together. In addition, when the measurement member 160/260/360 includes the second wavelength light source 164, the second wavelength camera sensor 165 needs to be included together. For example, the measurement member 160/260/360 furthers include the sprayer 161, the first wavelength light source 162, the first wavelength camera sensor 163, and the temperature sensor 166. Alternatively, the measurement member 160/260/360 includes one or more of the second wavelength light source 164, the second wavelength camera sensor 165, or the temperature sensor 166. In various modified examples as described above, when the measurement member 160/260/360 includes the sprayer 161, the first wavelength light source 162, and the first wavelength camera sensor 163, the display device performs steps S111, S112, and S113 of FIG. 21. When the measurement member 160/260/360 includes the second wavelength light source 164 and the second wavelength camera sensor 165, the display device performs steps S114 and S115 of FIG. 22. When the measurement member 160/260/360 includes the temperature sensor 166, the display device performs step S116 of FIG. 22.

In step S120, the processor 120 determines the degree of eyeball fatigue based on the measurement value of the measurement member 160/260/360.

In an embodiment, when the tear film breakage time of the user is determined to be less than a first criterion by comparing the tear film breakage time of the user with the first criterion, the degree of eyeball fatigue is high. For example, the first criterion may be 9 seconds.

In an embodiment, the processor 120 calculates an eye blink time interval using the number of eye blinks for a preset period. Next, the processor 120 calculates an eye protection index by dividing the tear film breakage time by the eye blink time interval, and determines that the degree of eyeball fatigue is high when the eye protection index is equal to or less than a preset criterion. For example, the preset criterion may be 1.

In an embodiment, the processor 120 compares the tear film breakage time of the user with the first criterion, compares the number of eye blinks for the preset period with a preset second criterion, and compares the difference in the temperature of the eyeball for the preset period with a third criterion, and determines that the degree of eyeball fatigue is high when one or more of the tear film breakage time of the user, the number of eye blinks for the preset period, or the difference in the temperature of the eyeball for the preset period deviates from the first criterion, the second criterion, or the third criterion. For example, the first criterion may be less than 9 seconds, the second criterion may be less than 8 times per minute, and the third criterion may be 0.3° or more.

In step S130, the processor 120 controls an intensity of a wavelength of the display member 150 based on the degree of eyeball fatigue. When the processor 120 determines that the degree of eyeball fatigue is high, the processor 120 increases an intensity of a red wavelength of the display member or decreases an intensity of a green wavelength and a blue wavelength of the display member. The red wavelength is greater than 600 nm.

When the processor 120 determines that the degree of eyeball fatigue is high, the processor 120 generates a signal that increases the intensity of the red wavelength of the display member or decreases the intensity of the green wavelength and the blue wavelength of the display member, and provide the generated signal to the display member 150. To this end, the processor 120 generates a control signal based on lookup table data for color characteristics according to a pre-stored input voltage.

In another modified example, as illustrated in FIG. 25, when the processor 120 determines that the degree of eyeball fatigue is high, the processor 120 outputs a pre-stored message through an input/output interface 140 (see FIGS. 1-3) for changing a screen color for reducing eyeball fatigue. The pre-stored message output through the input/output interface 140 includes a message prompt to the user for an input to change the screen color. In one embodiment, the message is displayed on a screen, but embodiments of the present disclosure are not necessarily limited thereto, and in an embodiment, the message is also audibly presented to the user through a speaker.

The user may or may not execute the screen color change that reduces eyeball fatigue through the input/output interface 140.

When the user inputs through the input/output interface 140 a selection to change the screen color to reduce eyeball fatigue, the processor 120 generates a signal for increasing the intensity of the red wavelength of the display member 150 or decreasing the intensity of the green wavelength and the blue wavelength of the display member 150, and transmits the generated signal to the display member 150. The red wavelength may be a wavelength that is greater than 600 nm. The green wavelength and blue wavelength may be wavelengths of 450 nm to 570 nm.

Embodiments of the present disclosure described above can be implemented as computer-readable code on a medium in which a program is recorded. The computer readable medium includes all kinds of recording devices in which data readable by a computer system is stored. Examples of computer-readable media include a hard disk drive (HDD), a solid state disk (SSD), a silicon disk drive (SDD), a ROM, a RAM, a CD-ROM, a magnetic tape, a floppy disk, an optical data storage device, etc. In addition, the computer includes a control unit of the display device. However, embodiments of the disclosure are not restricted to those forth herein. The above and other features of the disclosure will become more apparent to one of daily skill in the art to which the disclosure pertains by referencing the claims, with functional equivalents thereof to be included therein.

What is claimed is:
1. A head mounted display device, comprising:
a display member that displays an image;

a multi-channel lens unit disposed in a light path of light emitted from the display member;
a measurement member that measures a state of an eyeball that is viewing a video output through the multi-channel lens unit, the measurement member including a sprayer that sprays a contrast medium;
a first wavelength light source disposed outside the multi-channel lens unit and that emits a first wavelength light that increases a transmittance of the contrast medium;
a first wavelength camera sensor disposed outside the multi-lens lens unit wherein the first wavelength camera sensor generates a first video by receiving the first wavelength light emitted from the first wavelength light source and reflected from a user's eyeball, and measures a tear film breakage time of the user based on the first video; and
a processor that controls an intensity of a wavelength of light emitted from the display member by determining a degree of eyeball fatigue based on a measured value of the measurement member.
2. The head mounted display device of claim 1, wherein the contrast medium is fluorescein, and the first wavelength is in a range of 430 nm to 480 nm.
3. The head mounted display device of claim 1, wherein the processor determines that the degree of eyeball fatigue is high when the tear film breakage time is equal to or less than a preset reference time.
4. The head mounted display device of claim 3, wherein the processor increases an intensity of a red wavelength of the display member or decreases an intensity of a green wavelength and a blue wavelength of the display member when determining that the degree of eyeball fatigue is high.
5. The head mounted display device of claim 1, further comprising a sprayer holding member disposed on the display member, wherein the multi-channel lens unit is disposed on the sprayer and covers the sprayer and the sprayer holding member.
6. The head mounted display device of claim 5, wherein the multi-channel lens unit has a lens hole in a center, and the sprayer is disposed in the lens hole.
7. The head mounted display device of claim 6, wherein the multi-channel lens unit includes a concave rear surface that faces the display member, and
the sprayer is accommodated in a space between the rear surface of the multi-channel lens unit and the sprayer holding member.
8. The head mounted display device of claim 6, wherein the multi-channel lens unit further includes:
a plurality of sub-lenses that provide a plurality of channels, respectively, and are symmetrically disposed vertically and horizontally with respect to the lens hole; and
a plurality of reflective lenses disposed on rear surfaces of the plurality of sub-lenses and that overlap the sprayer.
9. The head mounted display device of claim 8, wherein the sprayer holding member includes a support ring, a plurality of leg portions connected to the support ring, and a sprayer holding portion connected to the plurality of leg portions,
the sprayer holding portion overlaps the lens hole, and
the plurality of leg portions overlap boundaries between the plurality of sub-lenses, respectively.
10. The head mounted display device of claim 8, wherein the sprayer includes an inner container that includes an accommodation space therein, an injector that moves the contrast medium in the inner container when receiving an electrical signal, and a funnel-type nozzle connected to the injector that discharges the contrast medium, wherein the funnel-type nozzle protrudes from the lens hole when the contrast medium is discharged.

11. The head mounted display device of claim 10, wherein the funnel-type nozzle includes a pipe portion connected to the inner container and a funnel portion that extends from the pipe portion, and the funnel portion has a taper angle with respect to a side surface of a pipe portion of the injector of 10° to 30°.

12. The head mounted display device of claim 1, wherein the measurement member further includes: a second wavelength light source disposed outside the multi-channel lens unit and that emits a second wavelength light; and a second wavelength camera sensor disposed outside the multi-channel lens unit, wherein the second wavelength camera sensor generates a second video by receiving the second wavelength light emitted from the second wavelength light source and reflected from the user's eyeball, and detects a number of eye blinks for a preset period based on the second video.

13. The head mounted display device of claim 12, wherein the second wavelength is in a range of 780 nm to 1000 nm.

14. The head mounted display device of claim 13, wherein the measurement member further includes a temperature sensor disposed outside the multi-channel lens unit, wherein the temperature sensor measures a temperature of the user's eyeball and calculates a temperature difference of the eyeball for a preset period.

15. The head mounted display device of claim 1, wherein the measurement member further includes a temperature sensor disposed outside the multi-channel lens unit, wherein the temperature sensor measures a temperature of the user's eyeball, and calculates a temperature difference of the eyeball for a preset period.

16. The head mounted display device of claim 12, wherein the processor determines the degree of eyeball fatigue by comparing the tear film breakage time and the number of eye blinks with each preset criterion.

17. The head mounted display device of claim 14, wherein the processor compares the tear film breakage time of the user, the number of eye blinks for the preset period, and the difference in the temperature of the eyeball with each respective preset criterion, and determines the degree of eyeball fatigue.

18. The head mounted display device of claim 16, wherein the processor compares the tear film breakage time of the user with a first criterion, compares the number of eye blinks for the preset period with a preset second criterion, and compares a temperature difference of the eyeball with a third criterion, and determines that the degree of eyeball fatigue is high when one or more of the tear film breakage time of the user, the number of eye blinks for the preset period, or the difference in the temperature of the eyeball deviates from the first criterion, the second criterion, or the third criterion.

19. A display device, comprising:
a display member that displays an image;
a multi-channel lens unit disposed in a light path of light emitted from the display member;
a lens rim that surrounds an edge of the multi-channel lens unit;
a sprayer that sprays a contrast medium;
a first wavelength light source disposed on the lens rim and that emits a first wavelength light that increases a transmittance of the contrast medium; and
a first wavelength camera sensor disposed on the lens rim, wherein the first wavelength camera sensor generates a first video by receiving the first wavelength light emitted from the first wavelength light source and reflected from a user's eyeball, and measures a tear film breakage time of the user based on the first video.

20. The display device of claim 19, further comprising:
a second wavelength light source disposed on the lens rim and that emits a second wavelength light; and
a second wavelength camera sensor disposed on the lens rim, wherein the second wavelength camera sensor generates a second video by receiving the second wavelength light emitted from the second wavelength light source and reflected from the user's eyeball, and detects a number of eye blinks for a preset period based on the second video.

21. The display device of claim 20, further comprising a temperature sensor disposed on the lens rim, wherein the temperature sensor measures a temperature of the user's eyeball, and calculates a temperature difference of the eyeball for a preset period.

22. The display device of claim 19, further comprising a temperature sensor disposed on the lens rim, wherein the temperature sensor measures a temperature of the user's eyeball, and calculates a temperature difference of the eyeball for a preset period.

23. The display device of claim 21, further comprising a processor that controls an intensity of light of a wavelength of the display member by comparing one or more of the tear film breakage time of the user, the number of eye blinks for the preset period, or the difference in the temperature of the eyeball with each respective preset criterion, and determining a degree of eyeball fatigue.

24. A method of controlling a head mounted display device, the control method comprising:
measuring, by a measurement member, a state of an eyeball that is viewing a video output from a display member and displayed through a multi-channel lens unit, the measurement member including a sprayer that sprays a contrast medium, a first wavelength light source, and a first wavelength camera sensor,
determining, by a processor, a degree of eyeball fatigue based on a measured value of the measurement member; and
controlling, by the processor, an intensity of light of a wavelength of the display member based on the degree of eyeball fatigue,
wherein measuring the state of the eyeball includes:
spraying, by the sprayer, the contrast medium from the sprayer according to a preset cycle;
generating, by the first wavelength camera sensor, a first video by receiving a the first wavelength light emitted from the first wavelength light source in response to the contrast medium and reflected from a user's eyeball; and
measuring, by the first wavelength camera sensor, a tear film breakage time of a user based on the first video.

25. The control method of claim 24, wherein the measurement member further includes a second wavelength light source and a second wavelength camera sensor, and measuring the state of the eyeball includes: generating, by the second wavelength camera sensor, a second video by receiving a second wavelength light emitted from the second wavelength light source and reflected from the user's eyeball; and detecting, by the second wavelength camera sensor, a number of eye blinks for a preset period based on the second video.

26. The control method of claim 25, wherein determining, by the processor, the degree of eyeball fatigue based on a measured value of the measurement member comprises:

calculating, by the processor, an eye blink time interval from a number of eye blinks for the preset period;

calculating, by the processor, an eye protection index by dividing the tear film breakage time by the eye blink time interval; and determining, by the processor, that the degree of eyeball fatigue is high when the eye protection index is equal to or less than a preset criterion.

27. The control method of claim 25, wherein the measurement member further includes a temperature sensor, and measuring the state of the eyeball further includes:

measuring, by the temperature sensor, a temperature of the user's eyeball; and calculating, by the temperature sensor, a difference in the temperature of the eyeball for a preset period.

28. The control method of claim 25, wherein determining, by the processor, the degree of eyeball fatigue based on a measured value of the measurement member comprises:

comparing, by the processor, the tear film breakage time of the user with a first criterion, comparing, by the processor, a number of eye blinks for the preset period with a preset second criterion;

comparing, by the processor, a difference in a temperature of the eyeball with a third criterion; and determining, by the processor, that the degree of eyeball fatigue is high when one or more of the tear film breakage time of the user, the number of eye blinks for the preset period, or the difference in the temperature of the eyeball deviates from the first criterion, the second criterion, or the third criterion.

29. The control method of claim 24, wherein controlling, by the processor, of the intensity of the wavelength of the display member based on the degree of eyeball fatigue comprises, when the processor determines that the degree of eyeball fatigue is high:

increasing, by the processor, an intensity of a red wavelength of the display member or decreasing an intensity of a green wavelength and a blue wavelength of the display member.

30. The control method of claim 24, wherein controlling, by the processor, of the intensity of the wavelength of the display member based on the degree of eyeball fatigue comprises, when the processor determines that the degree of eyeball fatigue is high:

outputting, by the processor, a pre-stored message through an input/output interface that notifies the user that the degree of eyeball fatigue is high and prompts the user for an input; and increasing, by the processor, an intensity of a red wavelength of the display member or decreasing, by the processor, an intensity of a green wavelength and a blue wavelength of the display member in response to the input from the user.

* * * * *